(12) United States Patent
Qiu et al.

(10) Patent No.: US 12,153,053 B2
(45) Date of Patent: Nov. 26, 2024

(54) UNBIASED AND HIGH-THROUGHPUT IDENTIFICATION AND QUANTIFICATION OF HOST CELL PROTEIN IMPURITIES BY AUTOMATED ITERATIVE LC-MS/MS (HCP-AIMS) FOR THERAPEUTIC PROTEIN DEVELOPMENT

(71) Applicant: Regeneron Pharmaceuticals, Inc., Tarrytown, NY (US)

(72) Inventors: Haibo Qiu, Millwood, NY (US); Yu Huang, Ossining, NY (US); Mengqi Hu, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 452 days.

(21) Appl. No.: 17/528,432

(22) Filed: Nov. 17, 2021

(65) Prior Publication Data

US 2022/0155317 A1    May 19, 2022

Related U.S. Application Data

(60) Provisional application No. 63/114,746, filed on Nov. 17, 2020.

(51) Int. Cl.
*G01N 30/72* (2006.01)
*G01N 30/68* (2006.01)
(Continued)

(52) U.S. Cl.
CPC ..... *G01N 33/6848* (2013.01); *G01N 30/7233* (2013.01); *G01N 30/8631* (2013.01);
(Continued)

(58) Field of Classification Search
CPC ...... H01J 49/0031; H01J 49/004; H01J 49/00; H01J 49/0027; H01J 49/0004;
(Continued)

(56) References Cited

U.S. PATENT DOCUMENTS

| | | | |
|---|---|---|---|
| 9,897,581 B1* | 2/2018 | Prakash | H01J 49/0031 |
| 2008/0111068 A1* | 5/2008 | Zabrouskov | H01J 49/004 |
| | | | 250/282 |
| 2010/0288917 A1* | 11/2010 | Satulovsky | H01J 49/0031 |
| | | | 250/281 |

FOREIGN PATENT DOCUMENTS

| | | | | |
|---|---|---|---|---|
| EP | 2955515 A1 * | 12/2015 | | G01N 27/624 |
| WO | WO-2012099971 A2 * | 7/2012 | | H01J 49/0036 |

OTHER PUBLICATIONS

Reisinger V, Toll H, Mayer RE, Visser J, Wolschin F., "A mass spectrometry-based approach to host cell protein identification and its application in a comparability exercise," Analytical Biochemistry, Jun. 17, 2014. (Year: 2014).*

(Continued)

*Primary Examiner* — Jeffrey P Aiello
(74) *Attorney, Agent, or Firm* — Kramer Levin Naftalis & Frankel LLP

(57) ABSTRACT

The present disclosure generally pertains to methods of identifying and quantitating host cell proteins (HCPs) in therapeutic protein development. In particular, the present invention generally pertains to methods of liquid chromatography-tandem mass spectrometry (LC-MS/MS) for unbiased identification and sensitive quantitation of HCPs in therapeutic protein development.

36 Claims, 10 Drawing Sheets

(51) Int. Cl.
  *G01N 30/86* (2006.01)
  *G01N 33/68* (2006.01)
  *H01J 49/00* (2006.01)
  *G01N 30/02* (2006.01)
(52) U.S. Cl.
  CPC ........ *H01J 49/0031* (2013.01); *H01J 49/004* (2013.01); *G01N 2030/027* (2013.01)
(58) Field of Classification Search
  CPC ........... G01N 33/6848; G01N 33/6851; G01N 33/6803; G01N 33/6842; G01N 33/68; G01N 2030/027; G01N 2030/8831; G01N 30/7233; G01N 30/8637; G01N 30/8631; G01N 30/72; G01N 30/8624; G01N 2800/60; G01N 2458/15; G01N 2560/00; G01J 3/28
  USPC ........ 73/61.52; 250/281; 435/7.1, 4; 436/86, 436/161, 173, 43; 702/28, 19, 22, 27, 23, 702/32, 30, 1, 179, 183; 703/11, 2
  See application file for complete search history.

(56) References Cited

OTHER PUBLICATIONS

Reisinger Veronika et al: "A mass spectrometry-based approach to host cell protein identification and its application in a comparability exercise", Analytical Biochemistry, Academic Press,Amsterdam, NL, vol. 463, Jun. 17, 2014 (Jun. 17, 2014), pp. 1-6, XP029059929, ISSN: 0003-2697.

Zhang Zhongqi: "Automated Precursor Ion Exclusion During LC-MS/MS Data Acquisition for Optimal Ion Identification", Journal of the American Society for Mass Spectrometry, [Online] vol. 23, No. 8, Aug. 1, 2012 (Aug. 1, 2012), pp. 1400-1407, XP55894438, US ISSN: 1044-0305, DOI: 10.1007/s13361-012-0401-3 Retrieved from the Internet: URL:https://pubs.acs.org/doi/pdf/10.1007/s13361-012-0401-3.

Briquet Sylvie et al: "Identification of Plasmodium falciparum nuclear proteins by mass spectrometry and proposed protein annotation", PLoS One, vol. 13, No. 10, Oct. 31, 2018 (Oct. 31, 2018), p. e0205596, XP055894722, DOI: 10.1371/journal.pone.0205596 Retrieved from the Internet: URL:https://journals.plos.org/plosone/article/file?id=10.1371/journal.pone.0205596&type=printable.

Huang Yu et al: "Toward unbiased identification and comparative quantification of host cell protein impurities by automated iterative LC-MS/MS (HCP-AIMS) for therapeutic protein development", Journal of Pharmaceutical and Biomedical Analysis, Elsevier B.V, Amsterdam, NL, vol. 200, Apr. 20, 2021 (Apr. 20, 2021), XP086569606,ISSN: 0731-7085, DOI: 10.1016/J.JPBA.2021.114069.

International Search Report, International Application No. PCT/US2021/059642, International Filing Date Nov. 17, 2021, Date of Mailing Mar. 7, 2022.

\* cited by examiner

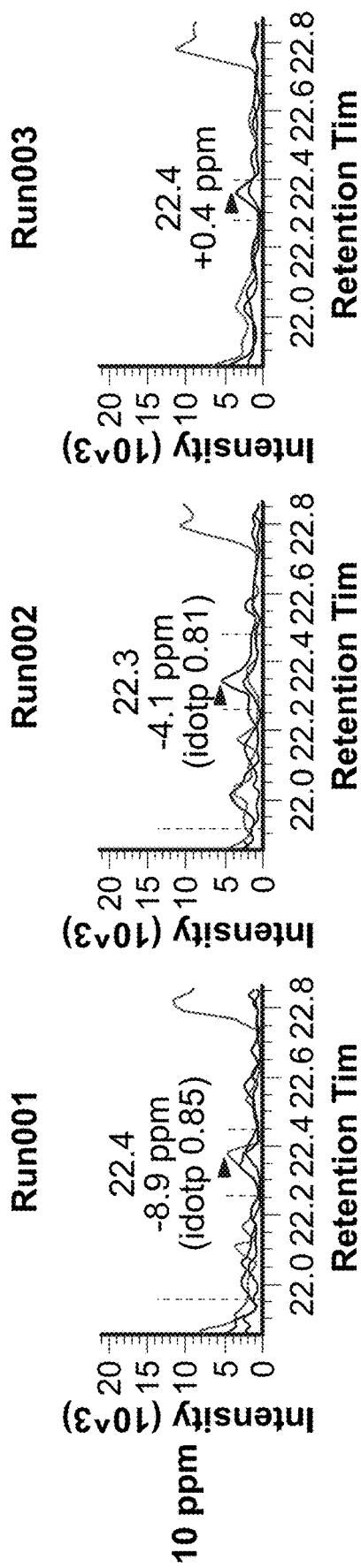
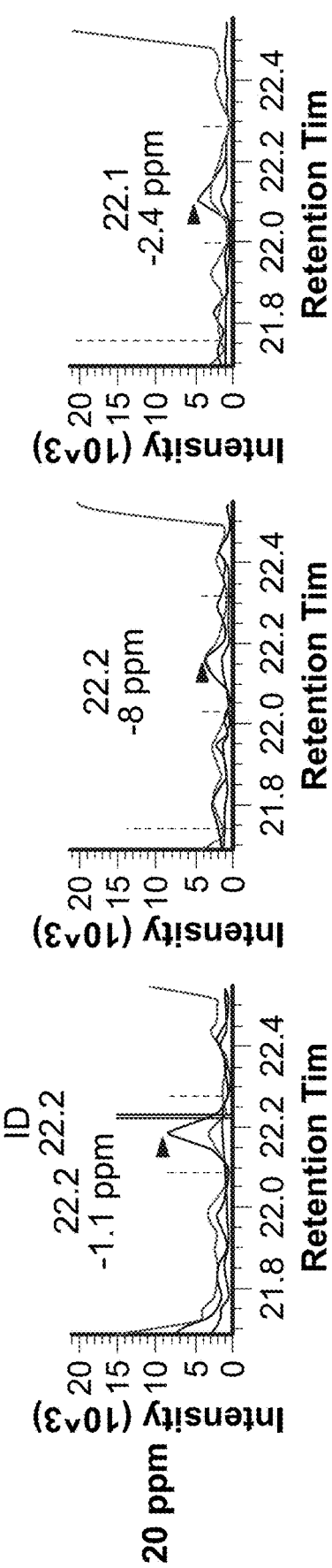
FIG. 4A, FIG. 4B, FIG. 4C, FIG. 4D, FIG. 4E, FIG. 4F

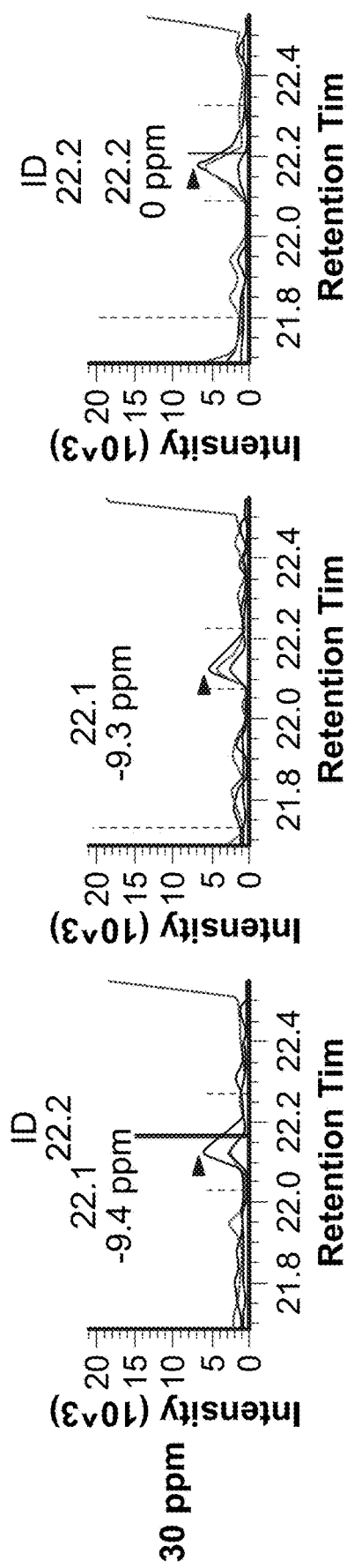
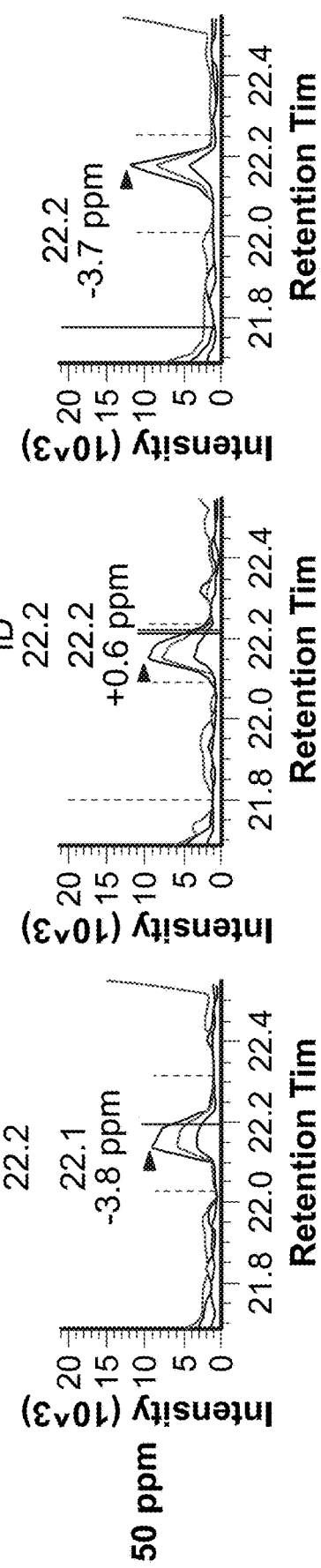

UNBIASED AND HIGH-THROUGHPUT IDENTIFICATION AND QUANTIFICATION OF HOST CELL PROTEIN IMPURITIES BY AUTOMATED ITERATIVE LC-MS/MS (HCP-AIMS) FOR THERAPEUTIC PROTEIN DEVELOPMENT

CROSS-REFERENCE TO RELATED APPLICATIONS

This application claims priority to and the benefit of U.S. Provisional Patent Application No. 63/114,746, filed Nov. 17, 2020 which is herein incorporated by reference.

FIELD

The present invention generally pertains to methods of identifying and quantitating host cell proteins (HCPs) in therapeutic protein development. In particular, the present invention generally pertains to methods of liquid chromatography-tandem mass spectrometry (LC-MS/MS) for identification and sensitive quantitation of HCPs in therapeutic protein development.

BACKGROUND

The presence of residual host cell proteins (HCPs) can cause potential safety risk for biopharmaceutical products and problems in manufacturing. Since recombinant DNA technology has been used widely for producing biopharmaceutical products in host cells, it is necessary to remove impurities to obtain biopharmaceutical products having high purity. Any residual impurities after conducting the purification bioprocesses should be present at an acceptably low level prior to conducting clinical studies. In particular, residual HCPs derived from mammalian expression systems, for example Chinese hamster ovary (CHO) cells, can compromise product safety, quality and stability. Even trace amounts of particular HCPs can sometimes cause an immunogenic response or an undesirable modification. Thus, host cell proteins in drug products and during the manufacturing process need to be monitored.

Liquid chromatography-tandem mass spectrometry (LC-MS/MS) has emerged as a powerful method for monitoring HCP impurities in process development and analytical characterization. However, there is usually a tradeoff between mass spectrometry-based methods that can deliver fast and unbiased HCP identification, versus in-depth and sensitive protein identification or accurate protein quantitation, due to differences in the complexity of sample preparation and LC-MS/MS methodologies.

It will be appreciated that a need exists for methods to identify and quantitate HCPs in pharmaceutical products, in a robust and unbiased fashion, to mitigate safety risks and optimize quality.

SUMMARY

Defining acceptable levels of HCP impurities has become a critical issue for using biological processing systems to manufacture biopharmaceutical products. There is a need to identify and characterize residual HCP impurities to optimize the safety and quality of therapeutic protein products. The present application provides methods to robustly identify and quantitate HCP impurities.

This disclosure provides a method for identifying at least one host cell protein (HCP) in a sample having the at least one HCP and at least another protein. In some exemplary embodiments, the method comprises (a) subjecting the sample to a chromatography column to obtain a chromatographic elution peak; (b) performing a tandem mass spectrometry analysis by performing a data-dependent acquisition cycle across the chromatographic elution peak, wherein the cycle includes: (i) obtaining a mass spectrum scan; (ii) selecting a plurality of precursor ions from the acquired mass spectrum scan as an automatic exclusion set; and (iii) obtaining a second mass spectrum scan after excluding the plurality of precursor ions set in the automatic exclusion set; and (c) using the obtained mass spectrum scans to identify the at least one HCP after the acquisition cycle is run for a predetermined number of times.

In one aspect, said predetermined number of cycles is one, two, three, four, or more cycles. In another aspect, a mass error tolerance for selecting a precursor ion for an automatic exclusion set is about 15 ppm. In another aspect, retention time tolerance for selecting a precursor ion for an automatic exclusion set is from about −0.2 minutes to about +0.4 minutes. In another aspect, the automatic exclusion set also includes at least one background ion. In yet another aspect, the automatic exclusion set includes at least one additional precursor ion not from the acquired mass spectrum scan. In yet another aspect, precursor ions from the acquired mass spectrum are not added to the automatic exclusion set if they fall below a predetermined intensity threshold.

In one aspect, the sample is prepared using direct digestion. In another aspect, the sample is prepared using native digestion. In another aspect, the sample is prepared using immunoprecipitation. In yet another aspect, the sample is prepared using activity-based protein profiling. In another aspect, the sample is prepared using fractionation. In another aspect, the sample is prepared using filtration.

In one aspect, the chromatography column comprises reverse phase liquid column, ion exchange column, size exclusion column, affinity column, hydrophobic interaction column, hydrophilic interaction column, mixed-mode column, or a combination thereof.

In one aspect, the sample comprises a protein of interest. In a specific aspect, the concentration of the protein of interest is at least 1000 times, at least 10,000 times, at least 100,000 times, or at least 1,000,000 times higher than a concentration of the at least one identified HCP. In yet another specific aspect, the protein of interest is an antibody, a bispecific antibody, an antibody fragment, a Fab region of an antibody, an antibody-drug conjugate, a fusion protein, or a drug.

In one aspect, the mass spectrometer is an electrospray ionization mass spectrometer, nano-electrospray ionization mass spectrometer, or a triple quadrupole mass spectrometer, wherein the mass spectrometer is coupled to a liquid chromatography system. In a specific aspect, the LC-MS/MS system is coupled with high field asymmetric waveform ion mobility spectrometry (FAIMS).

This disclosure also provides a method for quantitating at least one host cell protein (HCP) in a sample having the at least one HCP and at least another protein. In some exemplary embodiments, the method comprises (a) subjecting the sample to a chromatography column to obtain a chromatographic elution peak; (b) performing a tandem mass spectrometry analysis by performing a data-dependent acquisition cycle across the chromatographic elution peak, wherein the cycle includes: (i) obtaining a mass spectrum scan; (ii) selecting a plurality of precursor ions from the acquired mass spectrum scan as an automatic exclusion set; and (iii) obtaining a second mass spectrum scan after excluding the plurality of precursor ions set in the automatic exclusion set; and (c) using the obtained mass spectrum scans to quantitate the at least one HCP after the acquisition cycle is run for a predetermined number of times.

In one aspect, said predetermined number of cycles is one, two, three, four, or more cycles. In another aspect, a mass error tolerance for selecting a precursor ion for an automatic exclusion set is about 15 ppm. In another aspect, retention time tolerance for selecting a precursor ion for an automatic exclusion set is from about −0.2 minutes to about +0.4 minutes. In another aspect, the automatic exclusion set also includes at least one background ion. In yet another aspect, the automatic exclusion set includes at least one additional precursor ion not from the acquired mass spectrum scan. In yet another aspect, precursor ions from the acquired mass spectrum are not added to the automatic exclusion set if they fall below a predetermined intensity threshold.

In one aspect, the sample is prepared using direct digestion. In another aspect, the sample is prepared using native digestion. In another aspect, the sample is prepared using immunoprecipitation. In yet another aspect, the sample is prepared using activity-based protein profiling. In another aspect, the sample is prepared using fractionation. In another aspect, the sample is prepared using filtration.

In one aspect, the chromatography column comprises reverse phase liquid column, ion exchange column, size exclusion column, affinity column, hydrophobic interaction column, hydrophilic interaction column, mixed-mode column, or a combination thereof.

In one aspect, the sample comprises a protein of interest. In a specific aspect, the concentration of the protein of interest is at least 1000 times, at least 10,000 times, at least 100,000 times, or at least 1,000,000 times higher than a concentration of the at least one quantitated HCP. In yet another specific aspect, the protein of interest is an antibody, a bispecific antibody, an antibody fragment, a Fab region of an antibody, an antibody-drug conjugate, a fusion protein, or a drug.

In one aspect, the mass spectrometer is an electrospray ionization mass spectrometer, nano-electrospray ionization mass spectrometer, or a triple quadrupole mass spectrometer, wherein the mass spectrometer is coupled to a liquid chromatography system. In a specific aspect, the LC-MS/MS system is coupled with high field asymmetric waveform ion mobility spectrometry (FAIMS).

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 2A shows a base peak chromatogram (BPC) of three iterative MS/MS replicates (from top, middle to bottom panels, $1^{st}$, $2^{nd}$ and $3^{rd}$ MS BPC, respectively). FIG. 2B shows mass spectra from each iterative replication at the retention time denoted in FIG. 2A. Red diamonds indicate precursor ions selected for MS/MS scan in each of the iterative MS/MS runs.

FIGS. 4A-4L show the extracted ion chromatograms of three isotope transitions from PLBL2 peptide ions in different level of spike-in samples, with identification shown in Skyline as a vertical bar, according to an exemplary embodiment of the invention. FIGS. 4A-C illustrate 10 ppm of PLBL2 spike-in. FIGS. 4D-F illustrate 20 ppm of PLBL2 spike-in. FIGS. 4G-I illustrate 30 ppm of PLBL2 spike-in. FIGS. 4J-L illustrate 50 ppm of PLBL2 spike-in.

In FIGS. 5A and 5B, the upper bar plot shows the PSM from each replicate run; the lower Venn diagram shows the overlap of the PSM.

FIG. 7A shows the total MS1 area plot. FIG. 7B shows the retention time plot. FIG. 7C shows the precursor average mass error plot.

DETAILED DESCRIPTION

Figure 1A:
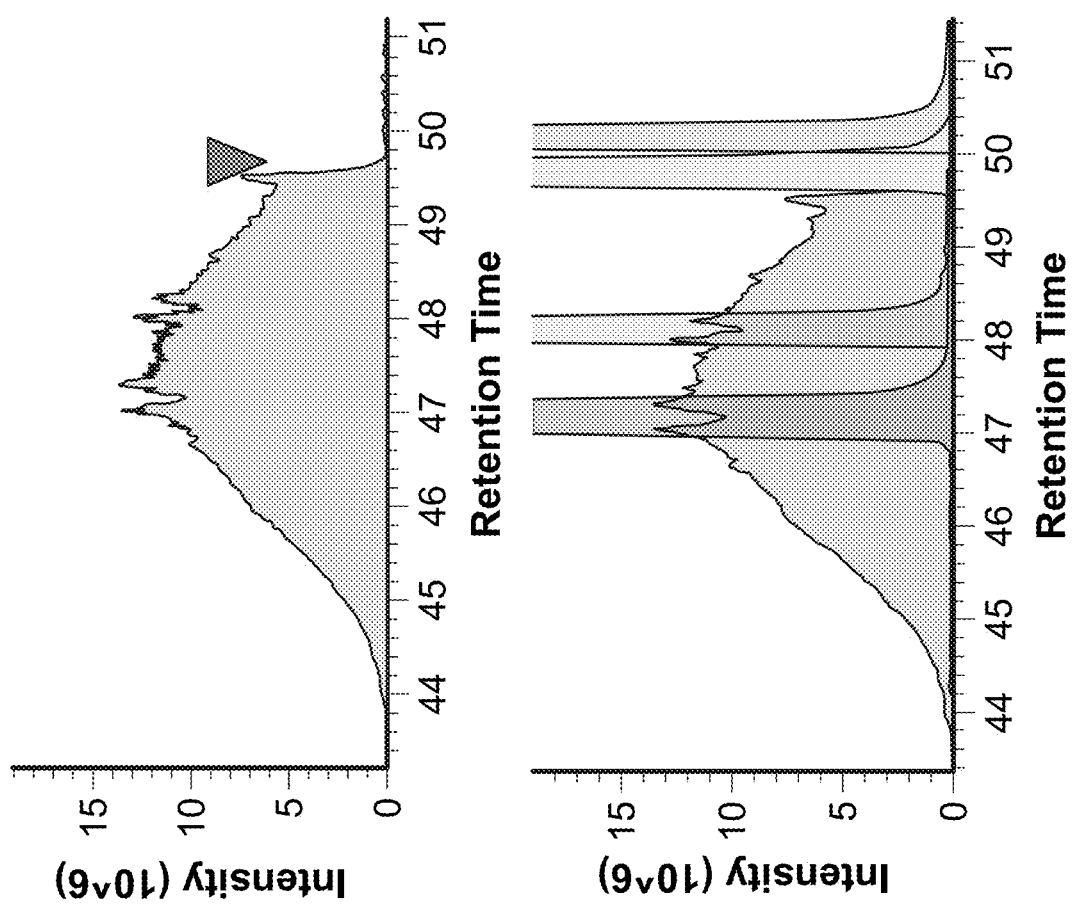
FIG. 1A shows an extracted ion chromatogram (EIC) illustrating interference of ion signal intensity due to the presence of other high abundance ions. The upper panel shows an EIC of a peptide with distorted peak shape, and the bottom panel shows EICs of several other peptides (shown in purple, blue, green, etc.) co-eluted with the peptide from upper panel.

Host cell proteins (HCPs) are process-related impurities originating from the production of therapeutic protein drugs. HCPs are normally a critical quality attribute at very low levels (typically under 100 ppm) that require in-depth purification development and a stringent control strategy for drug safety and efficacy (Hogwood et al., 2014, *Curr Opin Biotechnol*, 30:153-160). Residual HCPs may affect product safety via immunogenicity, toxicity, or unknown off-target enzymatic activity. They may affect product efficacy via impacts on drug stability, excipient stability, drug pharmacokinetics, or by competing with binding to an active site of a biological target. At different stages of drug development, the need for HCP analysis changes in characterization depth and sample set throughput (Hogwood et al., 2013, *Bioengineered*, 4:288-291; Zhu-Shimoni et al., 2014, *Biotechnol Bioeng*, 111:2367-2379). Development of a therapeutic protein expression cell line often generates hundreds to thousands of samples where HCPs might not be a critical issue. The following candidate cell line selection with purification step might need a total HCP assay to minimize the potential risk (Zhu-Shimoni et al.; Tscheliessnig et al., 2013, *Biotechnol J*, 8:655-670). During downstream purification process development, Design of Experiment (DOE) studies are typically performed to assess the relationship between process parameters and drug quality attributes, including HCPs. Although ELISA-based HCP assays have been widely used for quantitation, they lack a holistic profile and coverage for all the individual HCPs, where understanding of certain HCPs would be crucial to reduce the overall levels of HCPs (Falkenberg et al., 2019, *Biotechnol Prog*, 35:e2788). As a result, a relatively higher throughput and less biased HCP method is often needed to facilitate the purification development for HCP clearance.

A bottom-up proteomics workflow using liquid chromatography-tandem mass spectrometry (LC-MS/MS) has been widely used in the detailed identification of HCPs and in accurate quantitation of individual proteins (Zhu-Shimoni et al.; Bracewell et al., 2015, *Biotechnol Bioeng*, 112:1727-1737; Krawitz et al., 2006, *Proteomics*, 6:94-110; Gao et al., 2020, *Anal Chem*, 92:1007-1015; Reiter et al., 2019, *J Pharm Biomed Anal*, 174:650-654; Johnson et al., 2018, *Biologicals*, 52:59-66; Park et al., 2017, *Sci Rep*, 7:44246; Park et al., 2017, *Biotechnol Bioeng*, 114:2267-2278; Kreimer et al., 2017, *Anal Chem*, 89:5294-5302). However, there is usually a tradeoff between mass spectrometry-based methods that can deliver fast and unbiased HCP identification versus in-depth and sensitive protein identification or accurate protein quantitation, due to differences in the complexity of sample preparation and LC-MS/MS methodologies.

Direct digestion of protein samples for HCP analysis is almost always desired for HCP identification and quantitation. It generally requires minimal sample handling and as a result can maintain the quantitative profiles of individual HCPs. However, the broad dynamic range of drug versus host cell protein impurities represents a huge challenge for HCP identification by MS. For example, traditional proteomics methods such as data dependent acquisition (DDA) only fragment the most abundant precursors in a sample, and as a result usually miss low abundance host cell protein-related ions. DDA methods inherently bear some limitations for identification of proteins with large dynamic of abundance ranges. The limitation stems from the finite number of precursors chosen for MS2 scan in each MS1 scan, where "MS1" and "MS2" indicate the first and second mass analysis in tandem mass spectrometry respectively. Due to the actual duty cycle of the MS2 scans, some complex MS1 scans have very few precursor ions selection for MS2, leaving a large number of precursors not selected for MS2 identification. Besides, the fluctuation of low-level ions in a complex MS1 scan might result in stochastic precursor selection, leading to inconsistent or complementary identifications from each replication injection.

Alternatively, LC-MS/MS with data independent acquisition (DIA), particularly the SWATH method, has been shown as a promising strategy to simultaneously identify and quantitate proteins (Heissel et al., 2018, *Protein Expr Purif*, 147:69-77; Walker et al., 2017, *MAbs*, 9:654-663). Although the DIA-based method is able to generate a multiplexed MS2 from a window of precursor ions capturing MS2 fragments from theoretically all precursors, it still faces a small window dynamic range interference issue. In addition, a big hurdle is in data processing for effective and reliable protein identification, as well as the prerequisite of constructing a protein library. All of these challenges have limited the routine application of DIA in HCP analysis in drug development. DDA, therefore, still serves as the primary method for the initial identification of the peptides and proteins for most of the LC-MS/MS methods.

The recent development of a new MS acquisition method for deep proteomics, iterative precursor ion exclusion, has been shown to increase the depth of traditional tandem MS (Zhang, 2012, *J Am Soc Mass Spectrom*, 23:1400-1407; Wu et al., 2012, *Proteomics Clin Appl*, 6:304-308; Wang et al., 2008, *Anal Chem*, 80:4696-4710; Zhou, et al., 2015, *J Proteomics Bioinform*, 8:260-265). In an iterative fashion, the identification of new and unique peptide precursor ions would increase when other precursors that had already been selected for MS/MS fragmentation are excluded from further analysis. Iterative MS/MS is a straightforward acquisition method that could achieve identification and relative quantification of low-level HCPs without the need for enrichment.

To meet the challenges in HCP analysis, which entails fast turnaround time and robustness while mitigating potential risk of high levels of individual HCPs during process development and analytical characterization, described herein is a simple, robust and unbiased HCP analysis strategy utilizing an automated precursor ion exclusion (PIE) acquisition method, termed HCP-Automated Iterative MS or HCP-AIMS. This HCP-AIMS approach can use directly digested samples without requiring any enrichment or pre-treatment of the samples. With this HCP-AIMS strategy, low abundant HCP peptide precursor ions could be picked up for MS/MS identification in iterative replicates. Therefore, this approach is able to achieve deeper unbiased HCP identification compared to a normal data dependent acquisition (DDA) method to a detection limit of about 10 ppm or lower. At the same time, combining this method with the use of analytical flow UHPLC allows the entire HCP-AIMS workflow to be very robust, reproducible and suitable for high-throughput HCP analysis in therapeutic protein drug development and characterization.

Compared to the HCP analysis methods mentioned above, the HCP-AIMS workflow disclosed herein represents a simple, robust and sensitive approach suitable for higher throughput analysis with adequate protein identification and quantitation. The option of simple sample processing by direct digestion allows for plate-based digestion and automation for large-scale and high-throughput sample preparation. The automated iterative MS/MS acquisition enables fast and deep protein identification. Together with robust and highly consistent MS and regular flow LC system, the HCP-AIMS method is suitable to support process development, especially for the purpose of the DOE to determine the best process conditions for eliminating HCPs. The easy and simple sample preparation compatible with the HCP-AIMS workflow also allows fast and unbiased HCP identification and quantitation for drug candidate characterization, HCP out of specification (OOS) and out of trend (OOTs) investigations. This method serves as a robust and unbiased HCP assay, mitigating the risk of abundant problematic HCPs carried into final drug products, and ensuring the high quality of protein therapeutics in the clinic.

The present invention discloses a method for identifying and quantitating host cell proteins in therapeutic protein development.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one" and the terms "about" and "approximately" should be understood to permit standard variation as would be understood by those of ordinary skill in the art and where ranges are provided, endpoints are included. As used herein, the terms "include," "includes," and "including" are meant to be non-limiting and are understood to mean "comprise," "comprises," and "comprising" respectively.

As used herein, the term "database" refers to a bioinformatics tool, which provides for the possibility of searching the uninterpreted MS-MS spectra against all possible sequences in the database(s). Non-limiting examples of such tools are Mascot (http://www.matrixscience.com), Spectrum Mill (http://www.chem.agilent.com), PLGS (http://www.waters.com), PEAKS (http://www.bioinformaticssolutions.com), Proteinpilot (http://download.appliedbiosystems.com//proteinpilot), Phenyx (http://www.phenyx-ms.com), Sorcerer (http://www.sagenresearch.com), OMS SA (http://www.pubchem.ncbi.nlm.nih.gov/omssa/), X!Tandem (http://www.thegpm.org/TANDEM/), Protein Prospector (http://www.http://prospector.ucsfedu/prospector/mshome.htm), Byonic (https://www.proteinmetrics.com/products/byonic) or Sequest (http://fields.scripps.edu/sequest).

As used herein, the term "host cell proteins" (HCP) includes protein derived from a host cell and can be unrelated to the desired protein of interest. Host cell proteins can be a process-related impurity which can be derived from the manufacturing process and can include three major categories: cell substrate-derived, cell culture-derived and downstream-derived. Cell substrate-derived impurities include, but are not limited to, proteins derived from a host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables.

As used herein, the term "liquid chromatography" refers to a process in which a biological/chemical mixture carried by a liquid can be separated into components as a result of differential distribution of the components as they flow through (or into) a stationary liquid or solid phase. Non-limiting examples of liquid chromatography include reverse phase liquid chromatography, ion-exchange chromatography, size exclusion chromatography, affinity chromatography, hydrophobic interaction chromatography, hydrophilic interaction chromatography, or mixed-mode chromatography. In some aspects, the sample containing the at least one HCP can be subjected to any one of the aforementioned chromatographic methods or a combination thereof.

As used herein, the term "mass spectrometer" includes a device capable of identifying specific molecular species and measuring their accurate masses. The term is meant to include any molecular detector into which a polypeptide or peptide may be characterized. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends on the application. In some exemplary embodiments, the mass spectrometer can be a tandem mass spectrometer. As used herein, the term "tandem mass spectrometry" includes a technique where structural information on sample molecules is obtained by using multiple stages of mass selection and mass separation. A prerequisite is that the sample molecules be transformed into a gas phase and ionized so that fragments are formed in a predictable and controllable fashion after the first mass selection step. Multistage MS/MS, or MS$^n$, can be performed by first selecting and isolating a precursor ion (MS2), fragmenting it, isolating a primary fragment ion (MS3), fragmenting it, isolating a secondary fragment (MS4), and so on, as long as one can obtain meaningful information, or the fragment ion signal is detectable. Tandem MS has been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device. The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited, to sequencing amino acids of the protein fragments, determining protein sequencing, determining protein de novo sequencing, locating post-translational modifications, or identifying post translational modifications, or comparability analysis, or combinations thereof.

In some aspects, the mass spectrometer in the method or system of the present application can be an electrospray ionization mass spectrometer, nano-electrospray ionization mass spectrometer, or a triple quadrupole mass spectrometer, wherein the mass spectrometer can be coupled to a liquid chromatography system, wherein the mass spectrometer is capable of performing LC-MS (liquid chromatography-mass spectrometry) or a LC-MRM-MS (liquid chromatography-multiple reaction monitoring-mass spectrometry) analyses.

As used herein, the term "mass analyzer" includes a device that can separate species, that is, atoms, molecules, or clusters, according to their mass. Non-limiting examples of mass analyzers that could be employed are time-of-flight (TOF), magnetic electric sector, quadrupole mass filter (Q), quadrupole ion trap (QIT), orbitrap, Fourier transform ion cyclotron resonance (FTICR), and also the technique of accelerator mass spectrometry (AMS).

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus. In some exemplary embodiments, the electrospray ionization mass spectrometer can be a nano-electrospray ionization mass spectrometer.

As used herein, the term "protein" or "protein of interest" can include any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may comprise one or multiple polypeptides to form a single functioning biomolecule. A protein can include antibody fragments, nanobodies, recombinant antibody chimeras, cytokines, chemokines, peptide hormones, and the like. Proteins of interest can include any of biotherapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Darius Ghaderi et al., *Production platforms for biotherapeutic glycoproteins. Occurrence, impact, and challenges of non-human sialylation*, 28 BIOTECHNOLOGY AND GENETIC ENGINEERING REVIEWS 147-176 (2012), the entire teachings of which are herein incorporated). Proteins can be classified on the basis of compositions and solubility and can thus include simple proteins, such as globular proteins and fibrous proteins; conjugated proteins, such as nucleoproteins, glycoproteins, mucoproteins, chromoproteins, phosphoproteins, metalloproteins, and lipoproteins; and derived proteins, such as primary derived proteins and secondary derived proteins.

In some exemplary embodiments, the protein of interest can be a recombinant protein, an antibody, a bispecific antibody, a multispecific antibody, antibody fragment, monoclonal antibody, fusion protein, scFv and combinations thereof.

As used herein, the term "recombinant protein" refers to a protein produced as the result of the transcription and translation of a gene carried on a recombinant expression vector that has been introduced into a suitable host cell. In certain exemplary embodiments, the recombinant protein can be an antibody, for example, a chimeric, humanized, or fully human antibody. In certain exemplary embodiments, the recombinant protein can be an antibody of an isotype selected from group consisting of: IgG (e.g., IgG1, IgG2, IgG3, IgG4), IgM, IgA1, IgA2, IgD, or IgE. In certain exemplary embodiments the antibody molecule is a full-length antibody (e.g., an IgG1 or IgG4 immunoglobulin) or alternatively the antibody can be a fragment (e.g., an Fc fragment or a Fab fragment).

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. In different embodiments of the invention, the FRs of the anti-big-ET-1 antibody (or antigen-binding portion thereof) may be identical to the human germline sequences or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, for example, commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment comprises a sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively, or additionally, an antibody fragment may be wholly or partially synthetically produced. An antibody fragment may optionally comprise a single chain antibody fragment. Alternatively, or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The term "bispecific antibody" includes an antibody capable of selectively binding two or more epitopes. Bispecific antibodies generally comprise two different heavy chains with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions and such sequences can be expressed in a cell that expresses an immunoglobulin light chain.

A typical bispecific antibody has two heavy chains each having three heavy chain CDRs, followed by a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding of one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats such as, but not limited to, triomab, knobs into holes IgG (kih IgG), crossMab, orth-Fab IgG, Dual-variable domains Ig (DVD-Ig), two-in-one or dual action Fab (DAF), IgG-single-chain Fv (IgG-scFv), or κλ-bodies. The non-IgG-like different formats include tandem scFvs, diabody format, single-chain diabody, tandem diabodies (TandAbs), Dual-affinity retargeting molecule (DART), DART-Fc, nanobodies, or antibodies produced by the dock-and-lock (DNL) method (Gaowei Fan, Zujian Wang & Mingju Hao, Bispecific antibodies and their applications, 8 JOURNAL OF HEMATOLOGY & ONCOLOGY 130; Dafne Müller & Roland E. Kontermann, Bispecific Antibodies, HANDBOOK OF THERAPEUTIC ANTIBODIES 265-310 (2014), the entire teachings of which are herein incorporated).

As used herein "multispecific antibody" refers to an antibody with binding specificities for at least two different antigens. While such molecules normally will only bind two antigens (i.e., bispecific antibodies, bsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

In some exemplary embodiments, the protein of interest can be produced from mammalian cells. The mammalian cells can be of human origin or non-human origin, and can include primary epithelial cells (e.g., keratinocytes, cervical epithelial cells, bronchial epithelial cells, tracheal epithelial cells, kidney epithelial cells and retinal epithelial cells), established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LSI80 cells, LS174T cells, NCI-H-548 cells, RPMI2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PKi cells, PK(15) cells, GHi cells, GH3 cells, L2 cells, LLC-RC 256 cells, MHiCi cells, XC cells, MDOK cells, VSW cells, and TH-I, B1 cells, BSC-1 cells, RAf cells, RK-cells, PK-15 cells or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, Midi cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDMiC3 cells, KLN205 cells, McCoy cells, Mouse L cells, Strain 2071 (Mouse L) cells, L-M strain (Mouse L) cells, L-MTK' (Mouse L) cells, NCTC clones 2472 and 2555, SCC-PSA1 cells, Swiss/3T3 cells, Indian muntjac cells, SIRC cells, Cn cells, and Jensen cells, Sp2/0, NS0, NS1 cells or derivatives thereof).

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion.

One of the widely accepted methods for digestion of proteins in a sample involves the use of proteases. Many proteases are available and each of them have their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes—aspartic, glutamic, and metalloproteases, cysteine, serine, and threonine proteases, as classified on the mechanism of catalysis. The terms "protease" and "peptidase" are used interchangeably to refer to enzymes which hydrolyze peptide bonds.

Apart from contacting a host cell protein to a hydrolyzing agent, the method can optionally include steps for reducing the host cell protein, alkylating the host cell protein, buffering the host cell protein, and/or desalting the sample matrix. These steps can be accomplished in any suitable manner as desired.

In some exemplary embodiments, the method of identifying a host cell protein in a sample matrix can optionally comprise contacting a host cell protein to a protein reducing agent.

As used herein, the term "protein reducing agent" refers to the agent used for reduction of disulfide bridges in a protein. Non-limiting examples of protein reducing agents are dithiothreitol (DTT), ß-mercaptoethanol, Ellman's reagent, hydroxylamine hydrochloride, sodium cyanoborohydride, tris(2-carboxyethyl)phosphine hydrochloride (TCEP-HCl), or combinations thereof.

In some exemplary embodiments, the method of identifying a host cell protein in a sample matrix can optionally comprise contacting a host cell protein to a protein alkylating agent.

As used herein, the term "protein alkylating agent" refers to the agent used to alkylate certain free amino acid residues in a protein. Non-limiting examples of protein alkylating agents are iodoacetamide (IOA), chloroacetamide (CAA), acrylamide (AA), N-ethylmaleimide (NEM), methyl methanethiosulfonate (MMTS), and 4-vinylpyridine or combinations thereof.

In some exemplary embodiments, the method of identifying a host cell protein in a sample matrix can comprise denaturing a host cell protein, filtering the host cell protein using a molecular weight cut-off filter and identifying the host cell protein using a bottom-up or shotgun proteomics approach.

As used herein, "protein denaturing" can refer to a process in which the three-dimensional shape of a molecule is changed from its native state. Protein denaturation can be carried out using a protein denaturing agent. Non-limiting examples of a protein denaturing agent include heat, high or low pH, reducing agents like DTT (see below) or exposure to chaotropic agents. Several chaotropic agents can be used as protein denaturing agents. Chaotropic solutes increase the entropy of the system by interfering with intramolecular interactions mediated by non-covalent forces such as hydrogen bonds, van der Waals forces, and hydrophobic effects. Non-limiting examples for chaotropic agents include butanol, ethanol, guanidinium chloride, lithium perchlorate, lithium acetate, magnesium chloride, phenol, propanol, sodium dodecyl sulfate, thiourea, N-lauroylsarcosine, urea, and salts thereof.

In some exemplary embodiments, the method of identifying a host cell protein in a sample matrix can optionally comprise native digestion. As used herein, "native digestion" refers to digestion of proteins under non-denaturing conditions.

In some exemplary embodiments, the method for characterizing a host cell protein can optionally comprise enriching host cell proteins in the sample matrix by contacting the sample matrix with a chromatography support and performing a fractionation step. As used herein, the term "fractionation" can include a process of separating various peptides obtained from digesting the host cell proteins present in a sample matrix. The process can involve separating the peptides using an appropriate peptide fractionation technique(s) which can fractionate the peptides based on their various general properties such as the peptides' pI, hydrophobicity, metal binding ability, content of exposed thiol groups, size, charge, shape, solubility, stability and sedimentation velocity, ability to bind with various ionic groups, and affinity for substrates as a basis for isolating peptide(s) from complex biological sample matrixes. Peptides can also be separated based on their cellular location, thereby allowing the extraction of cytoplasmic, nuclear and membrane proteins.

In some exemplary embodiments, the method for characterizing a host cell protein can optionally comprise enriching host cell proteins in the sample matrix using immunoprecipitation (IP). As used herein, the term "immunoprecipitation" can include a process of precipitating a protein antigen out of solution using an antibody that specifically binds to that particular protein. Immunoprecipitation may be direct, in which antibodies for the target protein are immobilized on a solid-phase substrate, or indirect, in which free antibodies are added to the protein mixture and later captured with, for example, protein A/G beads.

In some exemplary embodiments, the method for characterizing a host cell protein can optionally comprise enriching host cell proteins in the sample matrix using activity-based protein profiling (ABPP). As used herein, the term "activity-based protein profiling" can include a process of immobilizing a target protein using an activity-based probe consisting of a reactive "warhead", a linker, and a tag. Non-limiting examples of probes include serine hydrolase probes including azido-FP, biotin-FP, desthiobiotin-FP, or TAMRA-FP, cysteine protease probes, or lipid probes. Non-limiting examples of tags include fluorophores, affinity tags or labeling tags.

As used herein, "sample," "sample matrix" or "biological sample" can be obtained from any step of the bioprocess, such as cell culture fluid (CCF), harvested cell culture fluid (HCCF), process performance qualification (PPQ), any step in the downstream processing, drug substance (DS), or a drug product (DP) comprising the final formulated product. In some other specific exemplary embodiments, the biological sample can be selected from any step of the downstream process of clarification, chromatographic production, viral inactivation, or filtration. In some specific exemplary embodiments, the drug product can be selected from manufactured drug product in the clinic, shipping, storage, or handling.

As used herein, the term "upstream process technology," in the context of protein preparation, refers to activities involving the production and collection of proteins from cells during or following the cell culture of a protein of interest. As used herein, the term "cell culture" refers to methods for generating and maintaining a population of host cells capable of producing a recombinant protein of interest, as well as the methods and techniques for optimizing the production and collection of the protein of interest. For example, once an expression vector has been incorporated into an appropriate host cell, the host cell can be maintained under conditions suitable for expression of the relevant nucleotide coding sequences, and the collection and production of the desired recombinant protein.

In some exemplary embodiments, the method of the present invention includes a predetermined number of cycles of tandem mass spectrometry analysis. In one aspect, the number of cycles is one, two, three, four, or more cycles. The number of cycles may be chosen depending on the needs of the user with regards to sample quantity, timing, number of peptide spectrum matches, quantification accuracy, or other needs which can be readily determined by one of ordinary skill in the art.

In some exemplary embodiments, the method of the present invention includes setting user-determined mass error tolerance and retention time exclusion tolerance to determine the addition of precursor ions to an automatic exclusion set. The mass error tolerance may be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 ppm, or another value according to the needs of the user, which can be readily determined by one of ordinary skill in the art. The retention time exclusion tolerance may be from −0.5 min, −0.4 min, −0.3 min, −0.2 min, −0.1 min, or 0 min to +0.8 min, +0.7 min, +0.6 min, +0.5 min, +0.4 min, +0.3 min, +0.2 min, +0.1 min, or 0 min, or another range according to the needs of the user, which can be readily determined by one of ordinary skill in the art.

In some exemplary embodiments, the method of the present invention includes generating an automatic exclusion set that is used to exclude precursor ions for ion fragmentation. In one aspect, precursor ions that are acquired in a mass spectrum scan are added to the automatic exclusion set. In another aspect, the automatic exclusion set also includes background ions. Background ions may be present in all mass spectrum scans and not representative of true peptide products. Background ions can be readily identified by one of ordinary skill in the art. In another aspect, the automatic exclusion set includes at least one additional precursor ion not from the acquired mass spectrum scan. A user may choose to predetermine at least one precursor ion that should not be fragmented even if it has not yet been acquired in a mass spectrum scan. In yet another aspect, precursor ions from the acquired mass spectrum are not added to the automatic exclusion set if they fall below a predetermined intensity threshold. A user may want to repeat a mass spectrum analysis of a precursor ion if a previous acquisition was of low quality or signal intensity.

In some exemplary embodiments, the method of the present invention includes a sample having at least one HCP and at least another protein. The relative concentration of the HCP may be expressed as parts per million, or ppm, relative to the concentration of another protein. The other protein may be a protein of interest. Thus, if an HCP in a sample including the HCP and a protein of interest is present at 1000 ppm, it is to be understood that the concentration of the protein of interest is 1000 times higher than the concentration of the HCP; if the HCP is present at 100 ppm, the concentration of the protein of interest is 10,000 times higher than the concentration of the HCP; and so forth.

It is understood that the present invention is not limited to any of the aforesaid database(s), host cell(s), protein denaturing agent(s), protein alkylating agent(s), protein reducing agent(s), instrument(s) used for identification, or chromatographic method(s), and any database(s), host cell(s), protein denaturing agent(s), protein alkylating agent(s), protein reducing agent(s), instrument(s) used for identification, or chromatographic method(s) can be selected by any suitable means.

Various publications, including patents, patent applications, published patent applications, accession numbers, technical articles and scholarly articles are cited throughout the specification. Each of these cited references is incorporated by reference herein, in its entirety and for all purposes.

The present invention will be more fully understood by reference to the following Examples. They should not, however, be construed as limiting the scope of the invention.

EXAMPLES

Materials. All chemicals were of high purity and obtained from commercial sources. Chromatography solvents were LCMS grade from Thermo Fisher Scientific (Waltham, MA). Monoclonal antibody and CHO proteins used in the spiked-in samples were produced in-house. Dithiothreitol (DTT) and tris(2-carboxyethyl) phosphine hydrochloride (TCEP) was purchased from Thermo Fisher Scientific. NIST monoclonal antibody standard, RM 8671, by the National Institute of Standards and Technology (Gaithersburg, MD) was obtained from Sigma-Aldrich.

Spike-in Sample Preparation. PLBL2 spike-in Samples: An aliquot of 1 μg of recombinant Chinese hamster phospholipase B-like 2 (PLBL2, UniProt ID: G316T1, produced by Regeneron) was spiked into 10 mg of monoclonal antibody drug substance (mAb 1 DS) sample in 10 mg/mL with no PLBL2 quantified previously to make a stock of 100 ppm PLBL2 spike-in sample. The stock was then diluted using the 10 mg/mL of the mAb1 DS to make 50 ppm, 30 ppm, 20 ppm and 10 ppm PLBL2 spike-in samples.

Multiple CHO protein spike-in dilution series: A total of 18 recombinant host cell proteins were first diluted and mixed into 1 nmol/mL for each of the protein. First level (Level 1) was prepared by adjusting the mAb DS to 10 mg/mL and spiking the mixture of the recombinant HCPs to 1% of the DS amount (mole:mole ratio) to a total volume of 200 μL. Level 2 to Level 7 were prepared using a 1:3 serial dilution method (50 μL of the previous level and 100 μL of 10 mg/mL mAb DS).

Direct Digestion of NIST mAb. An aliquot of 200 μg DS amount of the spike-in sample and NIST mAb (RM8671) was dried using a SpeedVac, then reconstituted with 20 μL of denaturing/reduction buffer containing 8 M urea and 10 mM dithiothreitol (DTT). The proteins were denatured and reduced at 37° C. for 30 min, and then incubated with 2 μL of 500 mM iodoacetamide for 30 min in the dark. Alkylated proteins were digested with 100 μL of 0.1 μg/μL trypsin at 37° C. for 4 hours. The peptide mixture was acidified with 10 μL of 20% formic acid. The concentration of the digested sample was about 1.51m/μL of protein equivalent.

Automated Iterative LC-MS/MS Analysis. The samples were analyzed using an Agilent 6545XL AdvanceBio LC/Q-TOF system. LC separation was performed on a Waters CSH column (2.1×150 mm, 1.7 μm) with 0.4 mL/min flow rate at 60° C. using a 60-minute LC method on the Agilent Infinity II UHPLC. The mobile phase buffer consisted of 0.1% FA in water (Buffer A), and the elution buffer consisted of 0.1% FA acetonitrile (ACN) (Buffer B). Peptides were eluted over a 50 minute linear gradient from 3% to 54% Buffer B five minutes after injection. A second isocratic pump with a 1:100 split line was used to deliver the mass reference solution for real time calibration running at 0.25 mL/minute (2.5 μL/minute into the ion source). The ion source was an Agilent Dual Jet Steam ESI source to simultaneously spray the LC effluent and the reference mass solution. Source drying gas temperature was set to 290° C. and 13 L/minute. Sheath gas was set to 275° C. and 12 L/minute. The nebulizer was set to 35 psi. In the MS acquisition setting, the first 3 minutes of LC was diverted to waste. From three minutes, the mass range of MS1 was set to 300-1700 m/z at 10 spectra/second acquisition rate. The MS/MS was set to 50-1700 m/z range at 3 spectra/second acquisition rate. The MS/MS isolation width was set to Narrow (~1.3 m/z). Acquisition mode was set to iterative MS/MS with mass error tolerance of 15 ppm and retention time exclusion tolerance of −0.2 min to +0.4 min. Each sample was injected three times at 24 μL each time using an Iterative MS/MS method.

QE Plus LC-MS/MS Analysis. The samples were analyzed using a Thermo Q Exactive Plus system. LC separation was performed on a Waters CSH column (2.1×150 mm, 1.7 μm) with 0.25 mL/minute flow rate at 60° C. using a 120-minute LC method on the Waters Acuity UPLC. The mobile phase buffer consisted of 0.1% FA in water (Buffer A), and the elution buffer consisted of 0.1% FA acetonitrile (ACN) (Buffer B). Peptides were eluted over a 90 minute linear gradient from 3% to 54% Buffer B five minutes after injection. The ion source was a regular HESI source. Probe heater temperature was set to 250° C. Capillary temperature was set to 350° C. and sheath gas was set to 40 units. The S-Lens RF level was set to 50. In the MS acquisition setting, the first three minutes of LC was diverted to waste. The DDA method used the Top 10 method. MS1 scan range was set to 200-2000 m/z range. The MS/MS isolation width was set to 3 m/z and NCE was set to 27. Minimum AGC target was set to 1e3. Each sample was injected three times at 24 μL each time.

Instrument Robustness Test. A total of 10 mg of mAb1 in 50 aliquots (each 200 μg) was digested using the direct digestion protocol as described above in a 96 well plate. All the digest was pooled into one vial and then aliquoted to 500 μL and stored in −80° C. for fresh injection each day. The injection runs were using the automated iterative MS/MS acquisition method. A total of 16 aliquots of the digestion run were finished in 25 days with a total of 312 injections and LC-MS/MS runs.

Data analysis. The raw data files were processed using Byonic from Protein Metrics Inc. The raw data files were searched against a Uniprot CHO K1 protein database that was concatenated with mAb protein sequences using Byonic. For NIST mAb, a UniprotKB mouse database with no redundant entries was used for the search. The search parameters included semi specific trypsin digestion, up to two missed cleavages, 20 ppm precursor mass tolerance, 30 ppm fragment mass tolerance, fixed cysteine alkylation, variable methionine oxidation, and asparagine deamidation. The Byonic result files were imported into Byologics and Skyline for further detailed analysis on a smaller set of protein sequences, and for result reporting. A minimum score of 350 for MS2 search was used to filter peptides.

Example 1. Signal and Column Saturation Limit

Figure 1B:
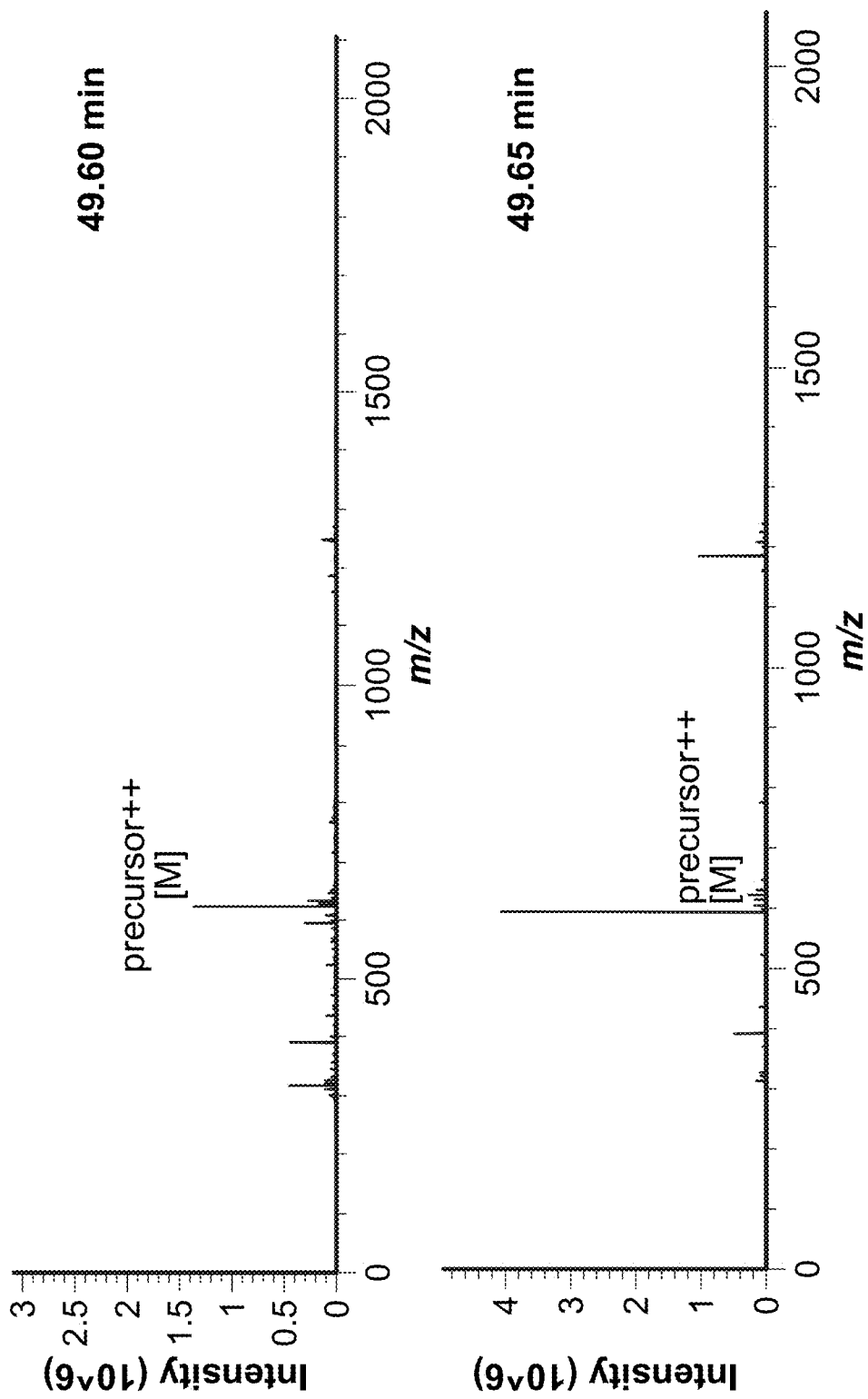
FIG. 1B shows a comparison of full mass spectra (MS1) of the selected peptide before and after the label point (red triangle) in panel A.

A major challenge in mass spectrometry-based HCP identification and quantitation is the comprehensive characterization of a large and diverse set of HCPs at very low abundance together with drug substance as the dominant presence (Doneanu et al., 2015, *Anal Chem*, 87:10283-10291; Schenauer et al., 2012, *Anal Biochem*, 428:150-157). To pinpoint the individual HCP peptides in the mixture of drug peptides, LC-MS/MS with data dependent acquisition (DDA) serves as the primary strategy for the initial identification of the peptides and proteins for most of the LC-MS methods. However, the intensity-based DDA methods inherently bear some limitations for identification of proteins with a large dynamic range in abundance. The limitation stems from the fact that there are a limited number of precursors chosen for MS2 scans after each MS1 scan. In addition, the ion filling effect of most trap type mass spectrometers limits the ion accumulation time of low abundant ions in the presence of other highly dominant ions under a given total number of ions and automatic gain control, as shown in FIG. 1. As a result, signal from low abundant HCP peptide ions coeluting with abundant drug peptides were suppressed (FIG. 1A) and could not be effectively captured from MS1 and therefore, could not be selected for MS2 fragmentation. In addition, ion suppression by abundant peptides also presents a signal limitation for accurate quantitation using MS1 spectra.

Figures 2A, 2B:
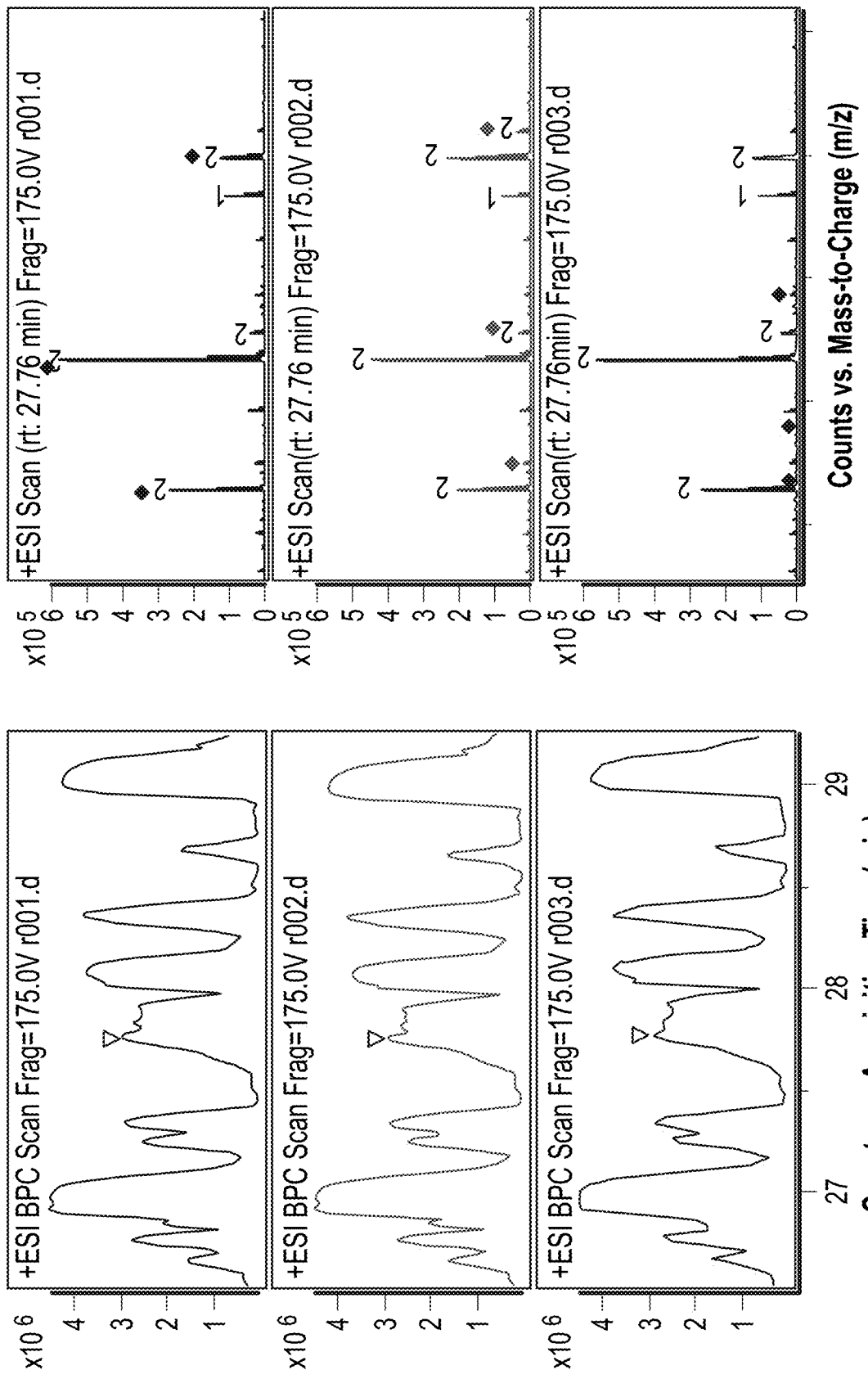
FIGS. 2A and 2B show the use of HCP-AIMS with automated iterative MS/MS runs and precursor selection according to an exemplary embodiment of the invention.

As an alternative to trap-based mass analyzers, time-of-flight (TOF) mass analyzers provide a linear and simple ion accumulation and acquisition strategy, which is less biased against low abundant ions in full MS1 acquisition. Herein, the Agilent 6545XT AdvanceBio Q-TOF system was employed, which provides a new iterative MS/MS data acquisition method for the HCP-AIMS workflow to improve identification of low-abundance HCP peptide precursor ions. Using this method, the protein digest sample underwent multiple LC-MS/MS injections and analysis. The first analysis was performed as a conventional DDA (Auto MS/MS in the Agilent instrument) run. In the following iterative LC-MS/MS injections, precursors that were previously selected for MS/MS fragmentation were automatically excluded on a rolling basis with customizable mass error tolerance and retention time exclusion tolerance. As a result, more unique and low abundance precursors were automatically picked up and interrogated by LC-MS/MS, as shown in FIG. 2.

Figures 3A, 3B:
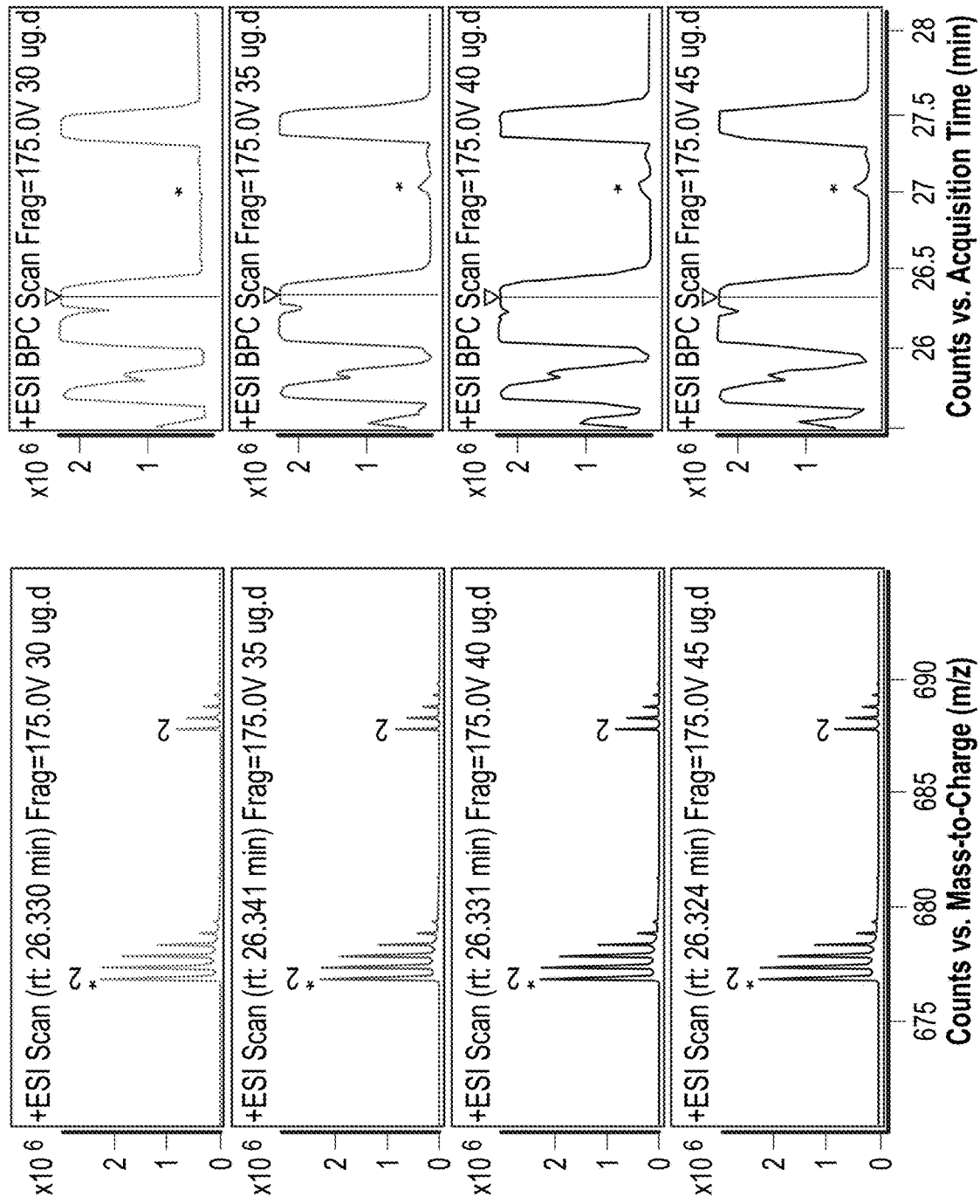
FIG. 3A shows mass spectra from the selected retention time, labelled in FIG. 3B by the open inverted triangle, according to an exemplary embodiment of the invention. Asterisks at the top of the isotope cluster indicate that ion counts reached the nonlinearity region.
FIG. 3B shows a base peak chromatogram of four runs with different loading amounts (30 to 45 µg, top panel to bottom panel) of digested protein injection according to an exemplary embodiment of the invention.
Figure 3C:
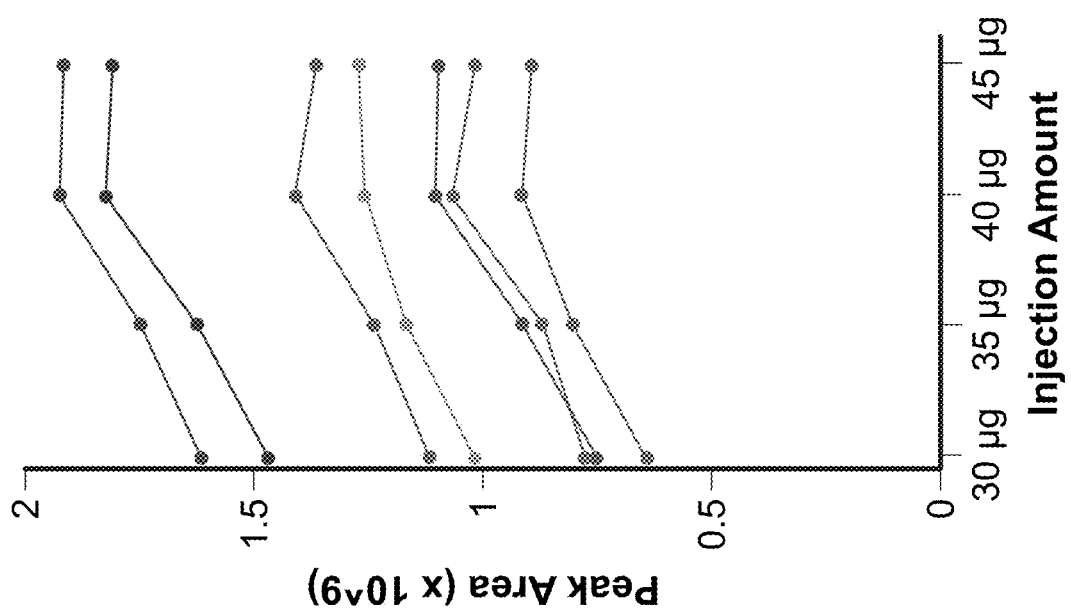
FIG. 3C shows peak area responses of seven selected peptides from these four runs with different loading amounts per injection according to an exemplary embodiment of the invention.

The TOF analyzer also allows moderate levels of signal saturation of dominant drug substance peptide ions without sacrificing the acquisition of low abundance HCP peptide ions. As a result, increasing the amount of sample injection would increase the abundance of HCP peptide ions, facilitating their identification and quantification. The 2.1 mm ID Waters CSH column was used to test the actual saturation limit of the system due to the increase of the injection amount. The Waters CSH column is widely used in LC-MS/MS analysis due to its high loading capacity and exceptional separation capability that does not deteriorate with high sample loading or when using MS-compatible formic acid in the mobile phase. In FIG. 3, injection amounts starting from 30 μg of protein digest were tested to determine the saturation limit of the system. Signal saturation from the detector of the most intense mass peaks started in the 30 μg injection, as indicated by the asterisk, shown in FIG. 3A. When base peak chromatograms were extracted, chromatographic peaks from drug substance peptides with the highest intensity had a flat plateau instead of the expected gaussian peak shape, further indicating signal saturation, shown in FIG. 3B. Even though signal saturation was observed starting from 30 μg for the most abundant peptides, the peak intensity of a low abundant peptide increased significantly, as shown for example in the peak at 27 min in FIG. 3B. The peak areas of extracted mass peaks with different relative abundances reached their maximum at 40 as shown in FIG. 3C, indicating a sample loading capacity for the column of approximately 40 μg.

Example 2. Identification of Spike-In HCPs in Drug Substance Samples

Single HCP spike-in at various levels: To evaluate HCP identification using the HCP-AIMS method and LC conditions established above, a single HCP spike-in test was first conducted. In this test, known amount of recombinant Chinese hamster PLBL2 protein was spiked into a PLBL2-free mAb drug substance (DS). Three replicate injections of each sample were analyzed with an iteratively generated exclusion list across each injection as described in the previous section. As shown in FIG. 4, for a series of 10~50 ppm (or ng HCP to mg of DS) of PLBL2 protein spike-in samples, identification of the PLBL2 protein was confirmed from one replicate of the 20 ppm spiked-in samples to multiple replicate identification for the 30 ppm and 50 ppm spike-in samples (shown as vertical bar with ID as label). A quick extraction from MS1 peak area can be used for quantification. Although the peak shape of the target peptide at the 10 ppm level may not be sufficient for accurate quantification, the extracted ion chromatograms (EICs) show that the MS1 ion chromatogram can be extracted as strong evidence of detection.

Multiple HCP dilution series: To further assess the sensitivity of the method across a larger set of proteins, another set of spike-in samples was made composed of 18 recombinant common host cell proteins, as shown in Table 1. All of these proteins were spiked into mAb drug substance at 1000 ppm as sample Level 1. The ppm calculation used here, marked by asterisks, was in molar ratio in order to better reflect the molecular ion population measured by mass spectrometry and to align with other quantitation in ppm calculation in the sections below. In comparison with the mass ratio that is typically used, for the same level of HCP, the value from the molar ratio is usually larger than the value from the mass ratio when the protein size is small (Table 1). A 1:3 serial dilution was made using Level 1 with mAb drug substance to generate a series of samples with various abundances of spiked-in proteins (from Level 2, 333 ppm to Level 7, 1.4 ppm). Compared to single run identification on Q Exactive Plus, where the identification limit of most proteins is at Level 3, 111.1 ppm (Table 3), the identification limit could reach to a further level of Level 4, 37 ppm for some of the proteins or some single peptides from these proteins using a TOF instrument with moderate signal saturation (Table 2). With replicate injections of iterative MS/MS, unique peptides identified from most levels are increased and more proteins are at an identification limit of Level 4, 37 ppm, with single peptide identification up to the next level of Level 5, 12.3 ppm. When converting the number to mass ratio ppm, for Level 4, the ppm values are at 2030 ppm (Table 1).

TABLE 1

Mass ratio ppm values corresponding to each molar ratio level

| | | | Dilution Levels | | | | | | |
|---|---|---|---|---|---|---|---|---|---|
| Accession | Protein Name | MW | Level1 1000* | Level2 333.3* | Level3 111.1* | Level4 37* | Level5 12.3* | Level6 4.1* | Level7 1.4* |
| G3GZB2 | Acid ceramidase | 42 kDa | 562.0 | 187.3 | 62.4 | 20.8 | 6.9 | 2.3 | 0.8 |
| G3I5L3 | Annexin | 35 kDa | 478.2 | 159.4 | 53.1 | 17.7 | 5.9 | 2.0 | 0.7 |
| G3HXN7 | Beta-hexosaminidase | 57 kDa | 766.1 | 255.3 | 85.1 | 28.3 | 9.4 | 3.1 | 1.1 |
| G3H8V5 | Carboxypeptidase | 51 kDa | 687.4 | 229.1 | 76.4 | 25.4 | 8.5 | 2.8 | 1.0 |
| G3H0L9 | Cathepsin B | 34 kDa | 462.5 | 154.1 | 51.4 | 17.1 | 5.7 | 1.9 | 0.6 |
| G3I4W7 | Cathepsin D | 41 kDa | 555.0 | 185.0 | 61.7 | 20.5 | 6.8 | 2.3 | 0.8 |
| G3INC5 | Cathepsin L1 | 34 kDa | 460.6 | 153.5 | 51.2 | 17.0 | 5.7 | 1.9 | 0.6 |
| Q9EPP7 | Cathepsin Z | 31 kDa | 419.9 | 140.0 | 46.7 | 15.5 | 5.2 | 1.7 | 0.6 |
| G3HNJ3 | Clusterin | 48 kDa | 653.0 | 217.7 | 72.6 | 24.2 | 8.0 | 2.7 | 0.9 |
| G3GUR1 | Complement C1r-A subcomponent | 68 kDa | 910.8 | 303.6 | 101.2 | 33.7 | 11.2 | 3.7 | 1.3 |
| A4URF0 | C-X-C motif chemokine | 8 kDa | 111.0 | 37.0 | 12.3 | 4.1 | 1.4 | 0.5 | 0.2 |
| G3IKC3 | Glutathione S-transferase Mu 6 | 69 kDa | 931.6 | 310.5 | 103.5 | 34.5 | 11.5 | 3.8 | 1.3 |
| G3H6V7 | Lipoprotein lipase | 47 kDa | 637.7 | 212.6 | 70.9 | 23.6 | 7.8 | 2.6 | 0.9 |
| G3HQY6 | Lysosomal acid lipase | 43 kDa | 573.8 | 191.2 | 63.7 | 21.2 | 7.1 | 2.4 | 0.8 |
| G3IBH0 | Metalloproteinase inhibitor 1 | 19 kDa | 265.5 | 88.5 | 29.5 | 9.8 | 3.3 | 1.1 | 0.4 |
| G3H533 | Peptidyl-prolyl cis-trans isomerase | 20 kDa | 279.3 | 93.1 | 31.0 | 10.3 | 3.4 | 1.1 | 0.4 |
| G3IIB1 | Sialate-O-Acetylesterase | 58 kDa | 784.5 | 261.5 | 87.2 | 29.0 | 9.6 | 3.2 | 1.1 |
| G3I4M9 | Transthyretin | 13 kDa | 177.3 | 59.1 | 19.7 | 6.6 | 2.2 | 0.7 | 0.2 |

TABLE 2

Unique peptide counts identified by Auto-MS/MS and Iterative MS/MS of each spike-in protein at various dilution levels (shown as Auto-MSMS/Iterative MS/MS)

| | | Dilution Levels (ppm) | | | | | | |
|---|---|---|---|---|---|---|---|---|
| Accession | Protein Name | Level1 1000 | Level2 333.3 | Level3 111.1 | Level4 37 | Level5 12.3 | Level6 4.1 | Level7 1.4 |
| G3GZB2 | Acid ceramidase | 10/26 | 8/15 | 3/7 | 0/1 | | | |
| G3I5L3 | Annexin | 10/28 | 6/17 | 2/9 | 0/3 | | | |
| G3HXN7 | Beta-hexosaminidase | 8/28 | 6/20 | 4/8 | 3/4 | | | |
| G3H8V5 | Carboxypeptidase | 7/20 | 6/13 | 1/2 | | | | |
| G3H0L9 | Cathepsin B | 8/20 | 4/10 | 1/3 | | | | |
| G3I4W7 | Cathepsin D | 6/21 | 3/11 | 4/8 | 2/4 | | | |
| G3INC5 | Cathepsin L1 | 4/13 | 2/5 | 2 | | | | |
| Q9EPP7 | Cathepsin Z | 4/13 | 3/7 | 1/3 | 1/3 | 0/1 | | |
| G3HNJ3 | Clusterin | 6/21 | 3/10 | 3/6 | 1/3 | | | |
| G3GUR1 | Complement C1r-A subcomponent | 8/38 | 9/25 | 5/10 | 0/2 | 0/1 | | |
| A4URF0 | C-X-C motif chemokine | 1/7 | 1/4 | 1/1 | 1/1 | | | |
| G3IKC3 | Glutathione S-transferase Mu 6 | 22/50 | 12/20 | 1/1 | 0/1 | 0/1 | | |
| G3H6V7 | Lipoprotein lipase | 2/5 | 3/4 | | | | | |
| G3HQY6 | Lysosomal acid lipase | 9/13 | 3/5 | | | | | |
| G3IBH0 | Metalloproteinase inhibitor 1 | 4/8 | 1/3 | 1/3 | 1/2 | | | |
| G3H533 | Peptidyl-prolyl cis-trans isomerase | 5/18 | 3/13 | 3/6 | 0/1 | | | |
| G3IIB1 | Sialate-O-Acetylesterase | 12/21 | 3/15 | 4/8 | 2/2 | | | |
| G3I4M9 | Transthyretin | 5/6 | 0/1 | | | | | |

TABLE 3

Unique peptide counts identified by a single injection run on Q Exactive Plus of each spike-in protein at various dilution levels

| | | Dilution Levels | | | | | | |
|---|---|---|---|---|---|---|---|---|
| Accession | Protein Name | Level1 1000 | Level2 333.3 | Level3 111.1 | Level4 37 | Level5 12.3 | Level6 4.1 | Level7 1.4 |
| G3GZB2 | Acid ceramidase | 17 | 13 | 4 | | | | |
| G3I5L3 | Annexin | 8 | 5 | 2 | | | | |
| G3HXN7 | Beta-hexosaminidase | 17 | 9 | 1 | | | | |
| G3H8V5 | Carboxypeptidase | 9 | 5 | 1 | | | | |
| G3H0L9 | Cathepsin B | 6 | 3 | 1 | | | | |
| G3I4W7 | Cathepsin D | 10 | 8 | 1 | | | | |
| G3INC5 | Cathepsin L1 | 6 | 4 | | | | | |
| Q9EPP7 | Cathepsin Z | 6 | 4 | 4 | | | | |
| G3HNJ3 | Clusterin | 13 | 8 | 3 | | | | |
| G3GUR1 | Complement Cir-A subcomponent | 12 | 12 | 6 | | | | |
| A4URF0 | C-X-C motif chemokine | 1 | 1 | 1 | | | | |
| G3IKC3 | Glutathione S-transferase Mu 6 | 29 | 20 | 8 | | | | |
| G3H6V7 | Lipoprotein lipase | 4 | 3 | | | | | |
| G3HQY6 | Lysosomal acid lipase | 9 | 7 | 2 | | | | |
| G3IBH0 | Metalloproteinase inhibitor 1 | 3 | 2 | | | | | |
| G3H533 | Peptidyl-prolyl cis-trans isomerase | 9 | 7 | 3 | | | | |
| G3IIB1 | Sialate-O-Acetylesterase | 9 | 6 | 1 | | | | |
| G3I4M9 | Transthyretin | 6 | 3 | 1 | | | | |

Figure 5B:
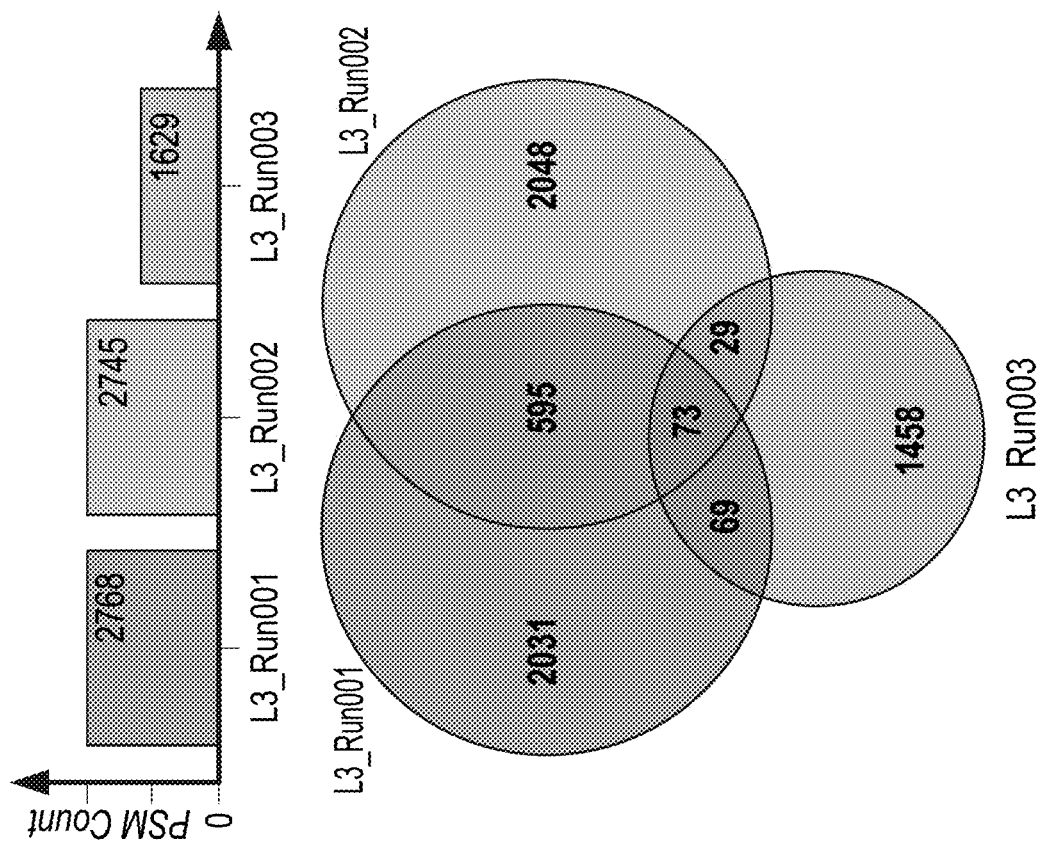
FIG. 5B shows a PSM comparison of three replicates from Iterative MS/MS for L3 according to an exemplary embodiment of the invention.
Figure 5A:
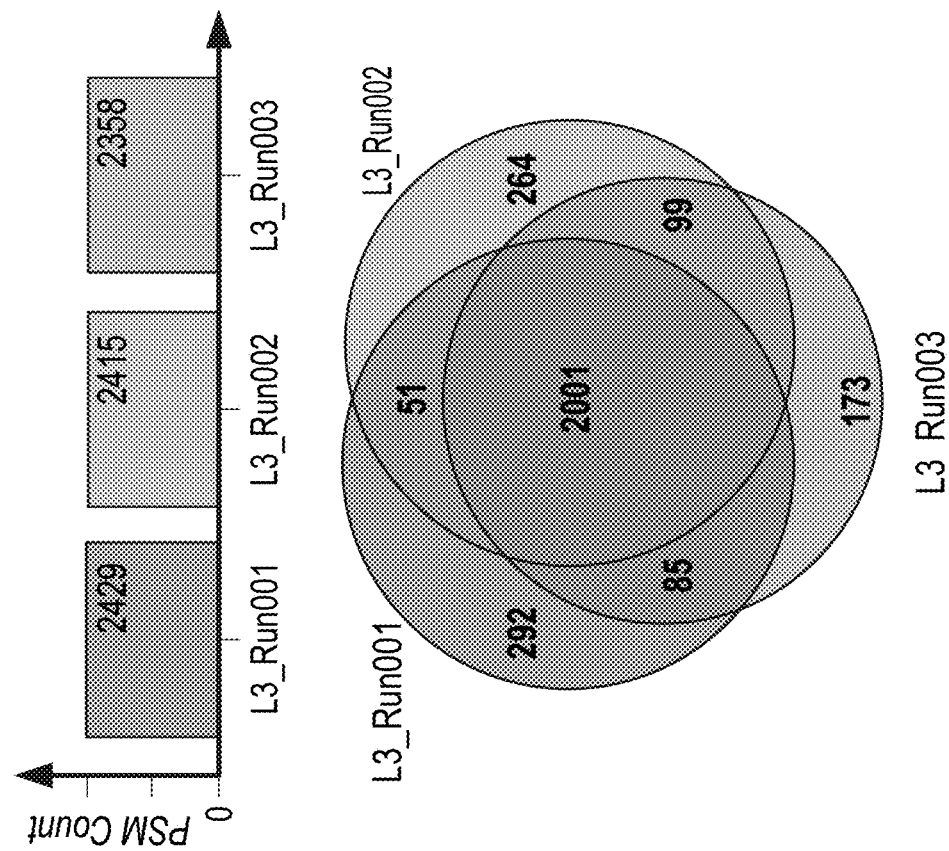
FIG. 5A shows a peptide spectrum match (PSM) comparison of three replicates from Auto-MS/MS for the spike-in protein Level 3 (L3) according to an exemplary embodiment of the invention.

The relationship between the number of peptide-spectrum matches (PSM) from 3 replicates of regular Auto MS/MS and iterative MS/MS are shown in FIG. 5A and FIG. 5B respectively. Compared to common PSM found in the regular replicate runs using Auto MS/MS, there were more unique PSM identified for each round of iterative MS/MS, resulting in more unique and complete identifications. Quick quantitation using MS1 EIC area from the top 3 peptides from each protein showed excellent linearity versus the spike-in concentration (Table 4) with low variations from the triplicate runs, also confirming that moderate saturation of DS signal did not affect the signals from the low level of host cell proteins.

TABLE 4

Linearity of quantitation with top 3 peptides of each protein from Level 1 to Level 4 by triplicate runs

| Accession | Protein Name | Mean of $R^2$ | Std Dev of $R^2$ |
|---|---|---|---|
| G3GZB2 | Acid ceramidase | 0.9682 | 0.0135 |
| G3I5L3 | Annexin | 0.9641 | 0.0186 |
| G3HXN7 | Beta-hexosaminidase | 0.9626 | 0.0185 |
| G3H8V5 | Carboxypeptidase | 0.9687 | 0.0168 |
| G3H0L9 | Cathepsin B | 0.9642 | 0.0187 |
| G3I4W7 | Cathepsin D | 0.9790 | 0.0116 |
| G3INC5 | Cathepsin L1 | 0.9670 | 0.0149 |
| Q9EPP7 | Cathepsin Z | 0.9766 | 0.0148 |
| G3HNJ3 | Clusterin | 0.9671 | 0.0137 |
| G3GUR1 | Complement C1r-A subcomponent | 0.9579 | 0.0193 |
| A4URF0 | C-X-C motif chemokine | 0.9727 | 0.0066 |
| G3IKC3 | Glutathione S-transferase Mu 6 | 0.9562 | 0.0125 |
| G3H6V7 | Lipoprotein lipase | 0.9499 | 0.0226 |
| G3HQY6 | Lysosomal acid lipase | 0.9575 | 0.0250 |
| G3IBH0 | Metalloproteinase inhibitor 1 | 0.9665 | 0.0146 |
| G3H533 | Peptidyl-prolyl cis-trans isomerase | 0.9628 | 0.0192 |
| G3IIB1 | Sialate O-acetylesterase | 0.9632 | 0.0162 |
| G3I4M9 | Transthyretin | 0.9736 | 0.0097 |

Example 3. Identification of HCPs from NIST mAb

To further evaluate the HCP-AIMS strategy, the method was applied to the NIST mAb standard. With direct digestion only and no enrichment steps, the sample preparation and data acquisition could be finished in a single day with no more than 200 μg of protein sample required. HCPs identified from the three replicates of the automated iterative MS/MS are shown in Table 5, with the maximum search score from the best peptides, count of PSM, number of unique peptides, and a semi-quantitation using the abundance from the best peptide of the host cell protein versus that from the NIST mAb (molar ratio ppm).

TABLE 5

Protein identification and quantification from automated iterative MS/MS runs of NIST mAb

| Accession | Protein Description | MaxScore | # PSM | # Unique peptide | Quant (ppm) |
|---|---|---|---|---|---|
| P05064 | Fructose-bisphosphate aldolase A | 810.94 | 24 | 10 | 243 |
| Q922R8 | Protein disulfide-isomerase A6 | 812.38 | 20 | 5 | 270.6 |
| P05063 | Fructose-bisphosphate aldolase C | 737.69 | 24 | 11 | 113.7 |
| P06745 | Glucose-6-phosphate isomerase | 538.77 | 5 | 3 | 67.6 |
| P01887 | Beta-2-microglobulin | 407.4 | 4 | 1 | 86.5 |
| Q99KN9 | Clathrin interactor 1 | 66.17 | 1 | 1 | 8.4 |
| Q8K4F5 | Protein ABHD11 | 221.27 | 3 | 3 | 9.2 |
| Q9EPX2 | Papilin | 272.61 | 5 | 2 | N/A |
| Q91YR9 | Prostaglandin reductase 1 | 169.04 | 1 | 1 | N/A |
| P08101 | Low affinity immunoglobulin gamma Fc region receptor II | 326.73 | 4 | 2 | 43.6 |
| Q03173 | Protein enabled homologue | 52.82 | 1 | 1 | N/A |
| P45878 | Peptidyl-prolyl cis-trans isomerase FKBP2 | 352.61 | 4 | 1 | 50.5 |

*(N/A showing MS1 level quantitation not available)

Compared to the previously reported microflow online 2D-LC method (Doneanu et al.) and native digestion sample preparation method (Doneanu et al.; Huang et al., 2017, *Anal Chem*, 89:5436-5444), the HCP-AIMS method covers all the shared HCPs from two previous studies with an approximate detection limit of 10 ppm, with several identified proteins that are at the 2-3 ppm range (mass ratio). Compared to the microflow online 2D-LC method, which involved fractionation and multiple microflow runs with a total run time of 500 minutes, the HCP-AIMS method uses a more robust 2.1 mm ID column and stable analytical flow with only 180 minutes run time for three replicates. The native digestion method has been shown as a very sensitive method and could reach an identification limit down to the single digit ppm level (Huang et al.). However, the method required a relatively larger amount of DS samples (1 mg or more) for effective accumulation of enough HCPs (Huang et al.). In addition, high temperature heating, centrifugation and sometimes filtration would limit its development towards high throughput analysis and single run quantitative analysis.

Figure 6:
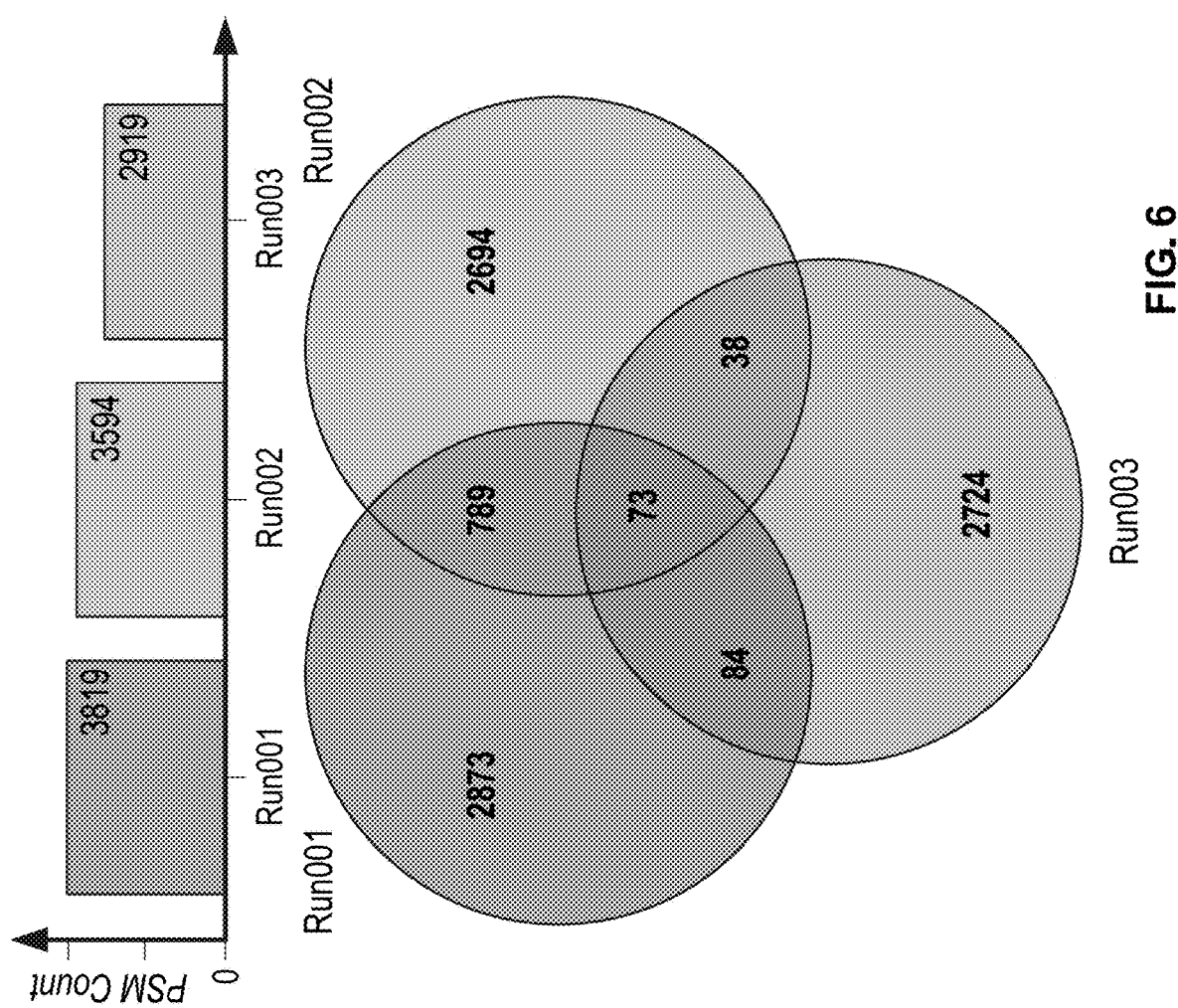
FIG. 6 shows the peptide-spectrum match (PSM) of three replicates of the automated iterative MS/MS of the NIST mAb sample according to an exemplary embodiment of the invention. The upper bar plot shows the PSM from each replicate run; the lower Venn diagram shows the overlap of the PSM.

Similar to the spike-in sample, the HCP PSM from three replicates of iterative MS/MS runs showed a large number of new unique PSMs in each subsequent replicate, as shown in FIG. 6. Also shown is a drop in the number of PSMs at the third replicate. For the Papilin, Prostaglandin reductase 1 and Protein enabled homologue, although they were identified from the protein search, due to the low unique peptide count and very limited number of the MS1 scans in the iterative run, no chromatogram peaks could be extracted for reliable quantitation.

Example 4. Robustness Assessment

Figures 7A, 7B, 7C:
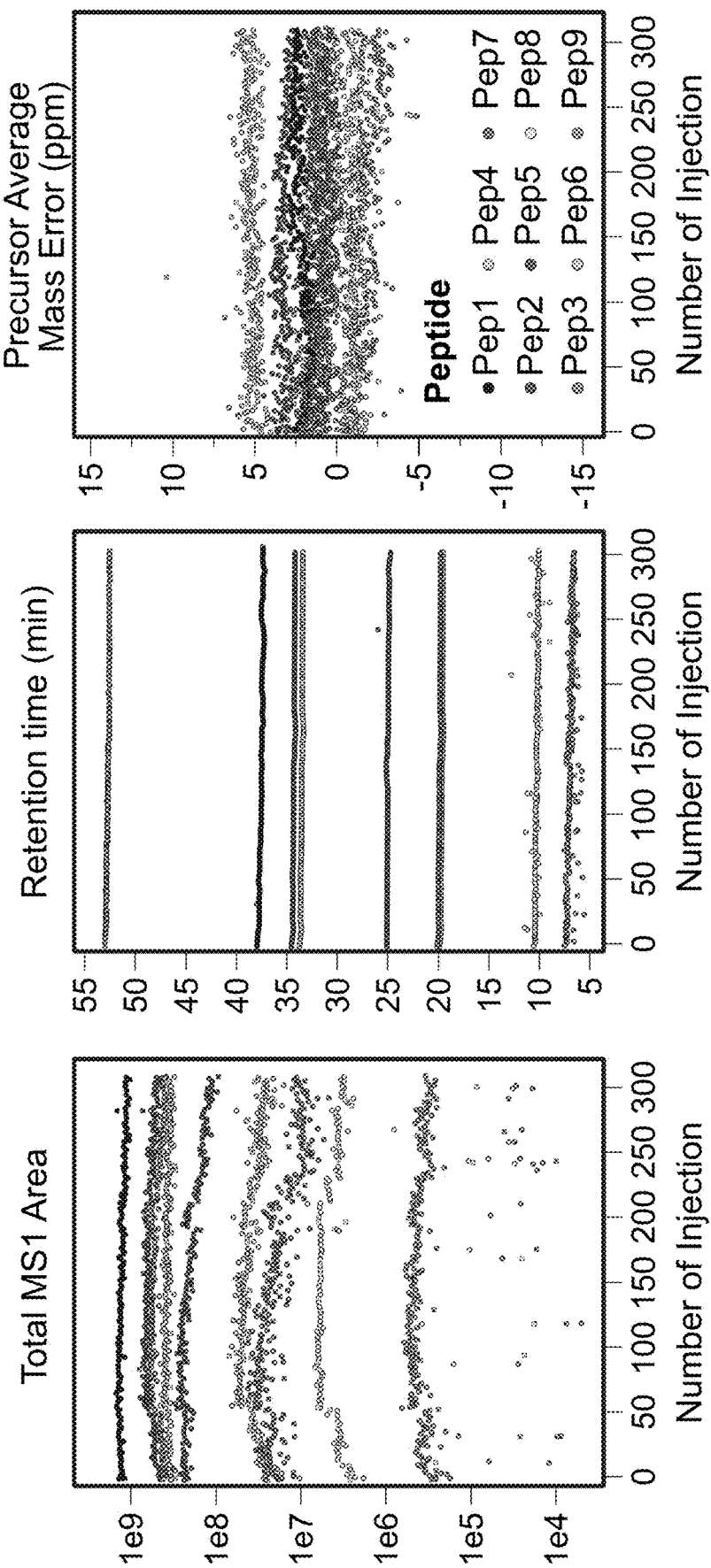
FIGS. 7A-7C show the performance metrics of the instrument robustness test of nine peptides from 300 injections according to an exemplary embodiment of the invention.

To meet the challenges of HCP analysis in drug development and deliver constant and reliable identification and quantitation of HCPs for large sample sets in a high-throughput analysis environment, the robustness of the HCP-AIMS assay and instrument stability are crucial, especially when injecting high dose of protein digests daily. To this end, a thorough test was performed to assess several key factors, such as signal intensity, retention time and mass error, which are essential for maintaining the effectiveness and robustness of the HCP-AIMS workflow. To ensure the consistency and high fidelity of the robustness test, the mAb DS test sample was digested in a large amount, then pooled and aliquoted into a single day injection volume for 20 injections. For a consecutive 3 weeks, the aliquot was taken from −80° C. storage and injected for testing. Representative peptides with intensity variation of four orders of magnitude were extracted to monitor the metrics for robustness, as shown in FIG. 7 and Table 6. Even with changes of solvents and accumulation of salts on the front ion source, the peak area from most peptides remained relatively stable over the 300 injections, with <30% coefficient of variation (CV) for the majority of the peptides. Due to high volume of direct injection over time, some early eluting peaks (such as glycopeptides) were not as stable as other peptides, with a higher deviation and max adjacent run difference. The retention time across the 300 injections was consistent for almost all the peptides with very tight adjacent run retention time stability. The saturation of some DS peptide peaks (Pep1-3) would affect the mass accuracy due to distorted ion statistics reflecting on the mass error toward the positive side. At the same time, other peptides maintained high mass accuracy for confident identification. In addition, even using a six-sigma rule, the range of the mass error didn't exceed the ~7 ppm range.

TABLE 6

Summary of the statistical analysis of the robustness metrics from 9 peptides

| Peptide | MS1 Peak Area | | Retention Time (min) | | | | | Precursor Mass Error (ppm) | | |
|---|---|---|---|---|---|---|---|---|---|---|
| | Mean Area | Area % CV | Upper 95% Mean | Lower 95% Mean | Mean Delta | Std Dev | Max Run to Run Variation | Mean Mass Error | Std Dev | 6σ Range |
| Pep1 | 1.32E+09 | 8.1 | 37.288 | 37.252 | 0.036 | 0.159 | 0.22 | 1.93 | 0.47 | (0.52, 3.34) |
| Pep2 | 6.12E+08 | 12.8 | 34.035 | 34.002 | 0.033 | 0.143 | 0.10 | 3.00 | 0.42 | (1.76, 4.25) |
| Pep3 | 5.11E+08 | 14.9 | 52.510 | 52.481 | 0.029 | 0.131 | 0.10 | 5.09 | 0.44 | (3.77, 6.40) |
| Pep4 | 3.84E+08 | 7.2 | 19.381 | 19.353 | 0.028 | 0.119 | 0.19 | 0.72 | 0.64 | (−1.20, 2.64) |
| Pep5 | 2.09E+08 | 24.2 | 24.596 | 24.562 | 0.034 | 0.150 | 0.16 | 1.46 | 0.47 | (0.06, 2.85) |
| Pep6 | 4.08E+07 | 27.1 | 33.222 | 33.194 | 0.029 | 0.128 | 0.14 | 0.57 | 0.47 | (−0.83, 1.98) |
| Pep7 | 2.04E+07 | 43.2 | 19.595 | 19.563 | 0.032 | 0.141 | 0.17 | 0.83 | 0.48 | (−0.60, 2.27) |
| Pep8 | 4.98E+06 | 27.1 | 9.956 | 9.903 | 0.053 | 0.231 | 0.40 | −1.11 | 0.63 | (−2.99, 0.77) |
| Pep9 | 4.23E+05 | 20.6 | 6.605 | 6.531 | 0.074 | 0.321 | 1.70 | −1.66 | 0.86 | (−4.25, 0.93) |

What is claimed is:

1. A method for identifying at least one host cell protein (HCP) in a sample having the at least one HCP and at least another protein, comprising:
   (a) subjecting the sample to a chromatography column to obtain a chromatographic elution peak;
   (b) performing a tandem mass spectrometry analysis including a data-dependent acquisition cycle across the chromatographic elution peak of (a), wherein the data-dependent acquisition cycle includes:
      (i) obtaining a mass spectrum scan;
      (ii) selecting a plurality of precursor ions from the obtained mass spectrum scan as an automatic exclusion set; and
      (iii) obtaining a second mass spectrum scan after excluding the plurality of precursor ions set in the automatic exclusion set
   (c) repeating steps (a) and (b) for a predetermined number of times; and
   (d) generating an output after steps (a) and (b) are run for a predetermined number of times, wherein the output identifies the at least one HCP.

2. The method of claim 1, wherein said predetermined number of cycles is one, two, three, four, or more cycles.

3. The method of claim 1, wherein a mass error tolerance for selecting a precursor ion for an automatic exclusion set is at about 15 ppm.

4. The method of claim 1, wherein a retention time tolerance for selecting a precursor ion for an automatic exclusion set is from about −0.2 minutes to about +0.4 minutes.

5. The method of claim 1, wherein the automatic exclusion set also includes at least one background ion.

6. The method of claim 1, wherein the automatic exclusion set includes at least one additional precursor ion not from the acquired mass spectrum scan.

7. The method of claim 1, wherein precursor ions from the acquired mass spectrum are not added to the automatic exclusion set if they fall below a predetermined intensity threshold.

8. The method of claim 1, wherein the sample preparation includes direct digestion.

9. The method of claim 1, wherein the sample preparation includes native digestion.

10. The method of claim 1, wherein the sample preparation includes immunoprecipitation.

11. The method of claim 1, wherein the sample preparation includes activity-based protein profiling.

12. The method of claim 1, wherein the sample preparation includes fractionation.

13. The method of claim 1, wherein the sample preparation includes filtration.

14. The method of claim 1, wherein the chromatography step comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

15. The method of claim 1, wherein the sample comprises a protein of interest.

16. The method of claim 15, wherein a concentration of the protein of interest is at least 1000 times, at least 10,000 times, at least 100,000 times, or at least 1,000,000 times higher than a concentration of the at least one identified HCP.

17. The method of claim 15, wherein the protein of interest is an antibody, a bispecific antibody, an antibody fragment, a Fab region of an antibody, an antibody-drug conjugate, a fusion protein, or a drug.

18. The method of claim 1, wherein the mass spectrometer is an electrospray ionization mass spectrometer, nano-electrospray ionization mass spectrometer, or a triple quadrupole mass spectrometer, wherein the mass spectrometer is coupled to a liquid chromatography system.

19. A method for quantitating at least one host cell protein (HCP) in a sample having the at least one HCP and at least another protein, comprising:
(a) subjecting the sample to a chromatography column to obtain a chromatographic elution peak;
(b) performing a tandem mass spectrometry analysis including a data-dependent acquisition cycle across the chromatographic elution peak of (a), wherein the data-dependent acquisition cycle includes:
(i) obtaining a mass spectrum scan;
(ii) selecting a plurality of precursor ions from the obtained mass spectrum scan as an automatic exclusion set; and
(iii) obtaining a second mass spectrum scan after excluding the plurality of precursor ions set in the automatic exclusion set;
(c) repeating steps (a) and (b) for a predetermined number of times; and
(d) generating an output after steps (a) and (b) are run for a predetermined number of times, wherein the output quantitates the at least one HCP.

20. The method of claim 19, wherein said predetermined number of cycles is one, two, three, four, or more cycles.

21. The method of claim 19, wherein a mass error tolerance for selecting a precursor ion for an automatic exclusion set is at about 15 ppm.

22. The method of claim 19, wherein a retention time tolerance for selecting a precursor ion for an automatic exclusion set is from about −0.2 minutes to about +0.4 minutes.

23. The method of claim 19, wherein the automatic exclusion set also includes at least one background ion.

24. The method of claim 19, wherein the automatic exclusion set includes at least one additional precursor ion not from the acquired mass spectrum scan.

25. The method of claim 19, wherein precursor ions from the acquired mass spectrum are not added to the automatic exclusion set if they fall below a predetermined intensity threshold.

26. The method of claim 19, wherein the sample preparation includes direct digestion.

27. The method of claim 19, wherein the sample preparation includes native digestion.

28. The method of claim 19, wherein the sample preparation includes immunoprecipitation.

29. The method of claim 19, wherein the sample preparation includes activity-based protein profiling.

30. The method of claim 19, wherein the sample preparation includes fractionation.

31. The method of claim 19, wherein the sample preparation includes filtration.

32. The method of claim 19, wherein the chromatography step comprises reverse phase liquid chromatography, ion exchange chromatography, size exclusion chromatography, affinity chromatography, hydrophobic interaction chromatography, hydrophilic interaction chromatography, mixed-mode chromatography, or a combination thereof.

33. The method of claim 19, wherein the sample comprises a protein of interest.

34. The method of claim 33, wherein a concentration of the protein of interest is at least 1000 times, at least 10,000 times, at least 100,000 times, or at least 1,000,000 times higher than a concentration of the at least one identified HCP.

35. The method of claim 33, wherein the protein of interest is an antibody, a bispecific antibody, an antibody fragment, a Fab region of an antibody, an antibody-drug conjugate, a fusion protein, or a drug.

36. The method of claim 19, wherein the mass spectrometer is an electrospray ionization mass spectrometer, nano-electrospray ionization mass spectrometer, or a triple quadrupole mass spectrometer, wherein the mass spectrometer is coupled to a liquid chromatography system.

* * * * *